US008071352B2

(12) United States Patent
Yoon et al.

(10) Patent No.: US 8,071,352 B2
(45) Date of Patent: Dec. 6, 2011

(54) **BACTERIOPHAGE HAVING KILLING ACTIVITY SPECIFIC TO *STAPHYLOCOCCUS AUREUS***

(75) Inventors: Seongjun Yoon, Seoul (KR); Sanghyeon Kang, Seoul (KR); Seabong Kyoung, Sungnam-Si (KR); Yunjaie Choi, Seoul (KR); Jeesoo Son, Seoul (KR)

(73) Assignee: Intron Biotechnology, Inc. (KR)

( * ) Notice: Subject to any disclaimer, the term of this patent is extended or adjusted under 35 U.S.C. 154(b) by 162 days.

(21) Appl. No.: 12/308,622

(22) PCT Filed: Jun. 20, 2007

(86) PCT No.: PCT/KR2007/002995
§ 371 (c)(1),
(2), (4) Date: May 27, 2009

(87) PCT Pub. No.: WO2007/148919
PCT Pub. Date: Dec. 27, 2007

(65) Prior Publication Data
US 2010/0267117 A1    Oct. 21, 2010

(30) Foreign Application Priority Data
Jun. 20, 2006    (KR) ........................ 10-2006-0055461

(51) Int. Cl.
*C12N 7/02*    (2006.01)
(52) U.S. Cl. ..................................... 435/235.1; 435/239
(58) Field of Classification Search .................. None
See application file for complete search history.

(56) References Cited

U.S. PATENT DOCUMENTS

| | | | | |
|---|---|---|---|---|
| 6,056,954 | A | 5/2000 | Fischetti | 424/94.1 |
| 6,056,955 | A | 5/2000 | Fischetti | 424/94.1 |
| 6,121,036 | A | 9/2000 | Ghanbari | 436/69.3 |
| 6,264,945 | B1 | 7/2001 | Fischetti | 424/94.1 |
| 6,432,444 | B1 | 8/2002 | Fischetti et al. | 424/443 |
| 7,572,602 | B1 | 8/2009 | Donovan | 435/69.7 |
| 7,582,291 | B2 | 9/2009 | Yoong | 424/93.6 |
| 2003/0152594 | A1 | 8/2003 | Pillich | 424/243.1 |
| 2003/0216338 | A1 | 11/2003 | Merril | 436/235.1 |
| 2004/0091470 | A1 | 5/2004 | Fischetti et al. | 424/94.6 |
| 2004/0146490 | A1 | 7/2004 | Kelly | 424/93.6 |
| 2005/0260171 | A1 | 11/2005 | Ghanbari et al. | 424/630 |
| 2007/0025978 | A1 | 2/2007 | Yoong | 424/93.6 |
| 2007/0077235 | A1 | 4/2007 | Loomis | 424/93.2 |
| 2010/0004321 | A1 | 1/2010 | Ross | 514/44 |
| 2010/0144619 | A1 | 6/2010 | Yoon et al. | 514/2.7 |
| 2010/0203019 | A1 | 8/2010 | Yoon et al. | 424/93.6 |
| 2010/0203180 | A1 | 8/2010 | Yoon et al. | 514/2 |
| 2010/0254950 | A1 | 10/2010 | Yoon et al. | 424/93.6 |

FOREIGN PATENT DOCUMENTS

| | | |
|---|---|---|
| KR | 2006-55461 | 6/2006 |
| KR | 2006-73562 | 8/2006 |
| KR | 2007-82358 | 8/2007 |
| KR | 1007-81669 | 12/2007 |
| WO | WO 03/067991 | 8/2003 |
| WO | WO 2004/020451 | 3/2004 |
| WO | WO 2004/062677 | 7/2004 |
| WO | WO 2006/063176 | 6/2006 |
| WO | WO 2007/148919 | 12/2007 |
| WO | WO 2008/016240 | 2/2008 |
| WO | WO 2009/035303 | 3/2009 |

OTHER PUBLICATIONS

Bokarewa MI, Jin T, Tarkowski A. (2006) *Staphylococcus aureus*: Staphylokinase. Int J Biochem Cell Biol. 38(4): 504-509.
KACC 97001P, titled "Staphlococcal Bacteriphase JS", deposited with the Korean Agricultural Culture Collection on Jun. 12, 2006.
International Search Report for PCT/KR2007/002995 (published as WO 2007/148919) dated Sep. 18, 2007, listing Yoon et al. as inventors and Intron Biotechnology, Inc. as Applicant.
International Preliminary Report on Patentability with Written Opinion for PCT/KR2007/002995 (published as WO 2007/148919) dated Dec. 22, 2008, listing Yoon et al. as inventors and Intron Biotechnology, Inc. as Applicant.
Accession No. KACC 97001P, Staphloccal bacteriophage, (2006).
Accession No. KCTC 11151BP, pBAD-TOPO-SAL1, (2007).
Accession No. KCTC 11152BP, *Escherichia coli* pBAD::Lysin, (2007).
Accession No. KCTC 11153BP, SAP1 bacteriophage, (2007).
Accession No. KCTC 11154BP, SAP2 bacteriophage, (2007).
Arciola CR, Baldassarri L, Montanaro L. (2001) Presence of icaA and icaD genes and slime production in a collection of staphylococcal strains from catheter-associated infections. J Clin Microbiol. 39(6): 2151-2156.
Arciola CR, Montanaro L, Baldassarri L, Borsetti E, Cavedagna D, Donati E. (1999) Slime production by Staphylococci isolated from prosthesis-associated infections. New Microbiol. 22(4): 337-341.
Bernhardt TG, Wang IN, Struck DK, Young R. (2002) Breaking free: "protein antibiotics" and phage lysis. Res Microbiol. 153(8): 493-501.
Cisani G, Varaldo PE, Grazi G, Soro O. (1982) High-level potentiation of lysostaphin anti-staphylococcal activity by lysozyme. Antimicrob Agents Chemother. 21(4): 531-535.
Costerton JW, Lewandowski Z, DeBeer D, Caldwell D, Korber D, James G. (1994) Biofilms, the customized microniche. J Bacteriol. 176(8): 2137-2142.
Cramton SE, Gerke C, Schnell NF, Nichols WW, Götz F. (1999) The intercellular adhesion (ica) locus is present in *Staphylococcus aureus* and is required for biofilm formation. Infect Immun. 67(10): 5427-5433.
Genbank Accession No. AA047477, titled "Soares pregnant uterus NbHPU", entered Sep. 19, 1996.
Genbank Accession No. AY176327, titled "*Staphylococcus* phage K, complete genome", Direct Submission (See O'Flaherty et al., 2004).
GenBank Accession No. AY954969, titled "Bacteriophage G1, complete genome", Direct Submission (See Kwan et al., 2005).

(Continued)

*Primary Examiner* — Zachariah Lucas
*Assistant Examiner* — Nicole Kinsey White
(74) *Attorney, Agent, or Firm* — Ballard Spahr LLP

(57) ABSTRACT

The present invention relates to a novel bacteriophage, more precisely a novel bacteriophage having killing activity specific to *Staphylococcus aureus* which is the causing agent of infectious diseases in human and animals, a pharmaceutical composition for the prevention and treatment of the disease caused by *Staphylococcus aureus*, an antibiotic and a disinfectant containing the bacteriophage as an active ingredient.

10 Claims, 9 Drawing Sheets

OTHER PUBLICATIONS

Graham S, Coote PJ. (2007) Potent, synergistic inhibition of *Staphylococcus aureus* upon exposure to a combination of the endopeptidase lysostaphin and the cationic peptide ranalexin. J Antimicrob Chemother. 59(4): 759-762.

Gründling A, Missiakas DM, Schneewind O. (2006) *Staphylococcus aureus* mutants with increased lysostaphin resistance. J Bacteriol. 188(17): 6286-6297.

Kusuma C, Jadanova A, Chanturiya T, Kokai-Kun JF. (2007) Lysostaphin-resistant variants of *Staphylococcus aureus* demonstrate reduced fitness in vitro and in vivo. Antimicrob Agents Chemother. 51(2): 475-482.

Kwan T, Liu J, DuBow M, Gros P, Pelletier J. (2005) The complete genomes and proteomes of 27 *Staphylococcus aureus* bacteriophages. Proc Natl Acad Sci USA. 102(14): 5174-5179.

Loessner MJ, Gaeng S, Scherer S. (1999) Evidence for a holin-like protein gene fully embedded out of frame in the endolysin gene of *Staphylococcus aureus* bacteriophage 187. J Bacteriol. 181(15): 4452-4460.

Loessner MJ. (2005) Bacteriophage endolysins—current state of research and applications. Curr Opin Microbiol. 8(4): 480-487.

Mah TF, O'Toole GA. (2001) Mechanisms of biofilm resistance to antimicrobial agents. Trends Microbiol. 9(1): 34-39.

Matsuzaki S, Rashel M, Uchiyama J, Sakurai S, Ujihara T, Kuroda M, Ikeuchi M, Tani T, Fujieda M, Wakiguchi H, Imai S. (2005) Bacteriophage therapy: a revitalized therapy against bacterial infectious diseases. J Infect Chemother. 11(5): 211-219.

Matsuzaki S, Yasuda M, Nishikawa H, Kuroda M, Ujihara T, Shuin T, Shen Y, Jin Z, Fujimoto S, Nasimuzzaman MD, Wakiguchi H, Sugihara S, Sugiura T, Koda S, Muraoka A, Imai S. (2003) Experimental protection of mice against lethal *Staphylococcus aureus* infection by novel bacteriophage phi MR11. J Infect.

McKenney D, Pouliot KL, Wang Y, Murthy V, Ulrich M, Döring G, Lee JC, Goldmann DA, Pier GB. (1999) Broadly protective vaccine for *Staphylococcus aureus* based on an in vivo-expressed antigen. 284(5419): 1523-1527.

O'Flaherty S, Coffey A, Edwards R, Meaney W, Fitzgerald GF, Ross RP. (2004) Genome of staphylococcal phage K: a new lineage of Myoviridae infecting gram-positive bacteria with a low G+C content. J Bacteriol. 186(9): 2862-2871.

O'Gara JP, Humphreys H. (2001) *Staphylococcus epidermidis* biofilms: importance and implications. J Med Microbiol. 50(7): 582-587.

Resch A, Fehrenbacher B, Eisele K, Schaller M, Götz F. (2005) Phage release from biofilm and planktonic *Staphylococcus aureus* cells. FEMS Microbiol Lett. 252(1): 89-96.

Sass P, Bierbaum G. (2007) Lytic activity of recombinant bacteriophage phi11 and phi12 endolysins on whole cells and biofilms of *Staphylococcus aureus*. Appl Environ Microbiol. 73(1): 347-352.

Schuch R, Nelson D, Fischetti VA. (2002) A bacteriolytic agent that detects and kills *Bacillus anthracis*. Nature. 418(6900): 884-889.

Severance PJ, Kauffman CA, Sheagren JN. (1980) Rapid identification of *Staphylococcus aureus* by using lysostaphin sensitivity. J Clin Microbiol. 11(6): 724-727.

Skurnik M, Strauch E. (2006) Phage therapy: facts and fiction. Int J Med Microbiol. 296(1): 5-14.

Vybiral D, Takác M, Loessner M, Witte A, von Ahsen U, Bläsi U. (2003) Complete nucleotide sequence and molecular characterization of two lytic *Staphylococcus aureus* phages: 44AHJD and P68. FEMS Microbiol Lett. 219(2): 275-283.

Waldvogel FA. (2000) Infections Associated with Indwelling Medical Devices, pp. 55-88, 2000, ASM, Washington, DC.

Walencka E, Sadowska B, Rózalska S, Hryniewicz W, Rózalska B. (2006) *Staphylococcus aureus* biofilm as a target for single or repeated doses of oxacillin, vancomycin, linezolid and/or lysostaphin. Folia Microbiol (Praha). 51(5): 381-386.

Wu JA, Kusuma C, Mond JJ, Kokai-Kun JF. (2003) Lysostaphin disrupts *Staphylococcus aureus* and *Staphylococcus epidermidis* biofilms on artificial surfaces. Antimicrob Agents Chemother. 47(11): 3407-3414.

Yoong P, Schuch R, Nelson D, Fischetti VA. (2004) Identification of a broadly active phage lytic enzyme with lethal activity against antibiotic-resistant *Enterococcus* faecalis and *Enterococcus* faecium. J Bacteriol. 186(14): 4808-4812.

International Search Report issued Mar. 20, 2009 for WO 2009/035303 published on Mar. 19, 2009 (Application No. PCT/KR2008/005434 filed on Sep. 12, 2008) (Inventors—Yoon et al.; Applicant—Intron Biotechnology, Inc.).

Written Opinion issued Mar. 20, 2009 for WO 2009/035303 published on Mar. 19, 2009 (Application No. PCT/KR2008/005434 filed on Sep. 12, 2008) (Inventors—Yoon et al.; Applicant—Intron Biotechnology, Inc.).

International Preliminary Report on Patentability issued Mar. 16, 2010 for WO 2009/035303 published on Mar. 19, 2009 (Application No. PCT/KR2008/005434 filed on Sep. 12, 2008) (Inventors—Yoon et al.; Applicant—Intron Biotechnology, Inc.).

International Preliminary Report on Patenability issued Dec. 22, 2008 for WO 2007/148919 published on Dec. 27, 2007 (Application No. PCT/KR2007/002995 filed on Jun. 20, 2007) (Inventors—Yoon et al.; Applicant—Intron Biotechnology, Inc.).

International Search Report issued Sep. 18, 2007 for WO 2007/148919 published on Dec. 27, 2007 (Application No. PCT/KR2007/002995 filed on Jun. 20, 2007) (Inventors—Yoon et al.; Applicant—Intron Biotechnology, Inc.).

Written Opinion issued Sep. 18, 2007 for WO 2007/148919 published on Dec. 27, 2007 (Application No. PCT/KR2007/002995 filed on Jun. 20, 2007) (Inventors—Yoon et al.; Applicant—Intron Biotechnology, Inc.).

International Preliminary Report on Patentability issued Feb. 10, 2009 for WO 2008/016240 published on Feb. 7, 2008 (Application No. PCT/KR2007/003629 filed on Jul. 27, 2007) (Inventors—Yoon et al.; Applicant—Intron Biotechnology, Inc.).

International Search Report issued Oct. 30, 2007 for WO 2008/016240 published on Feb. 7, 2008 (Application No. PCT/KR2007/003629 filed on Jul. 27, 2007) (Inventors—Yoon et al.; Applicant—Intron Biotechnology, Inc.).

Written Opinion issued Oct. 30, 2007 for WO 2008/016240 published on Feb. 7, 2008 (Application No. PCT/KR2007/003629 filed on Jul. 27, 2007) (Inventors—Yoon et al.; Applicant—Intron Biotechnology, Inc.).

Notice of Allowance with Examiner Interview Summary issued Jun. 1, 2011 for U.S. Appl. No. 12/378,457, filed Feb. 12, 2009 (Inventors—Yoon et al.).

Final Rejection issued Apr. 28, 2011 for U.S. Appl. No. 12/378,457, filed Feb. 12, 2009 (Inventors—Yoon et al.).

Response after Non-Final Office Action filed Feb. 25, 2011 for U.S. Appl. No. 12/378,457, filed Feb. 12, 2009 (Inventors—Yoon et al.).

Non-Final Rejection issued Oct. 26, 2010 for U.S. Appl. No. 12/378,457, filed Feb. 12, 2009 (Inventors—Yoon et al.).

Preliminary Amendment filed Dec. 19, 2008 for U.S. Appl. No. 12/308,627, filed Jun. 15, 2009) (Inventors—Yoon et al.).

Restriction Requirement mailed by the U.S. Patent and Trademark Office on Sep. 12, 2011 for U.S. Patent Appl. No. 12/378,365, which was filed on Feb. 12, 2009 (Inventors—Yoon et al.) (pp. 1-5).

Issue Notification mailed by the U.S. Patent and Trademark Office on Oct. 5, 2011 for U.S. Appl. No. 12/378,457, which was filed on Feb. 12, 2009 (Inventors—Yoon et al.) (p. 1).

Notice of Allowance mailed by the U.S. Patent and Trademark Office on Aug. 8, 2011 for U.S. Appl. No. 12/378,457, which was filed on Feb. 12, 2009 (Inventors—Yoon et al.) (pp. 1-7).

Non-Final Office Action mailed by the U.S. Patent and Trademark Office on Sep. 1, 2011 for U.S. Appl. No. 12/308,627, which was filed on Jun. 15, 2009 (Inventors—Yoon et al.) (pp. 1-21).

Fenton M, Casey PG, Hill C, Gahan CG, Ross RP, McAuliffe O, O'Mahony J, Maher F, Coffey A. (2010) The truncated phage lysin CHAP(k) eliminates *Staphylococcus aureus* in the nares of mice. Bioeng Bugs. 1(6): 404-407.

Jain A, Agarwal A. (2009) Biofilm production, a marker of pathogenic potential of colonizing and commensal *staphylococci*. J Microbiol Methods. 76(1): 88-92.

[Fig.1]
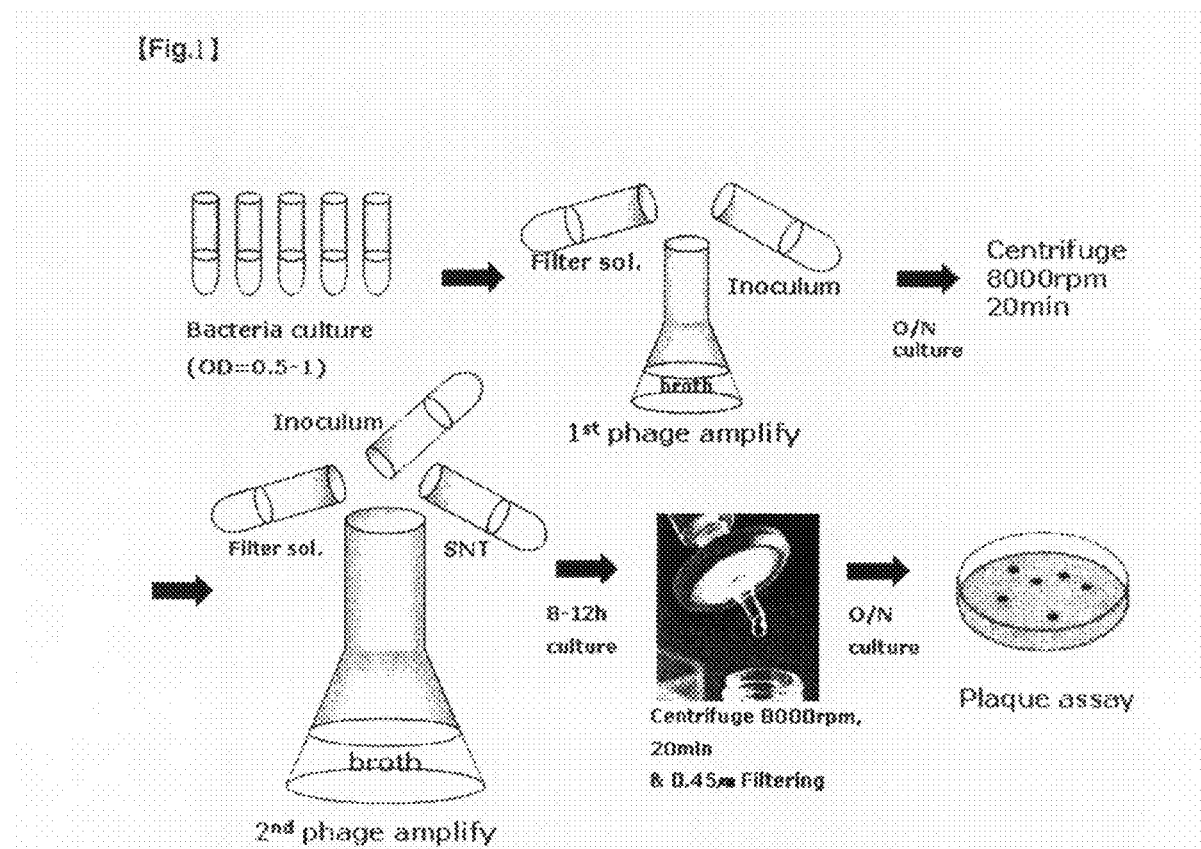
[Fig.2]
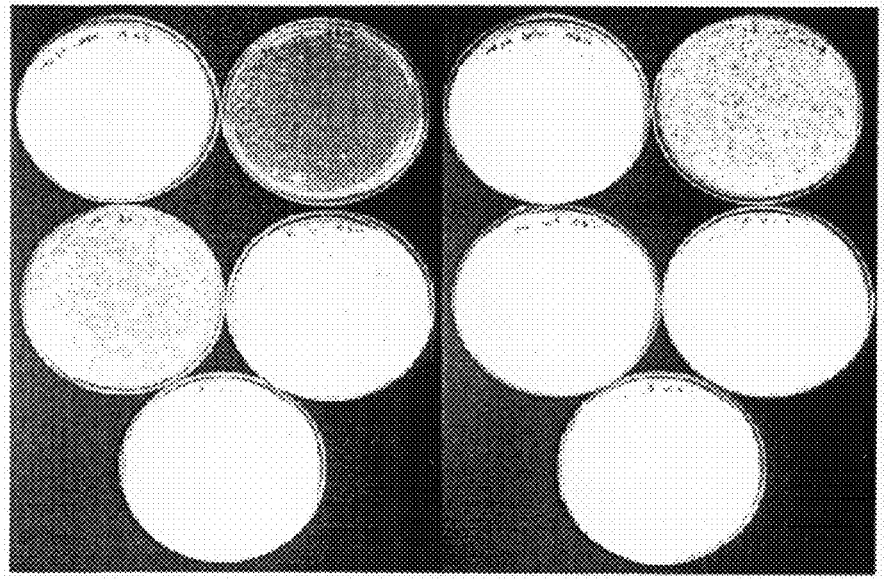

[Fig.3]
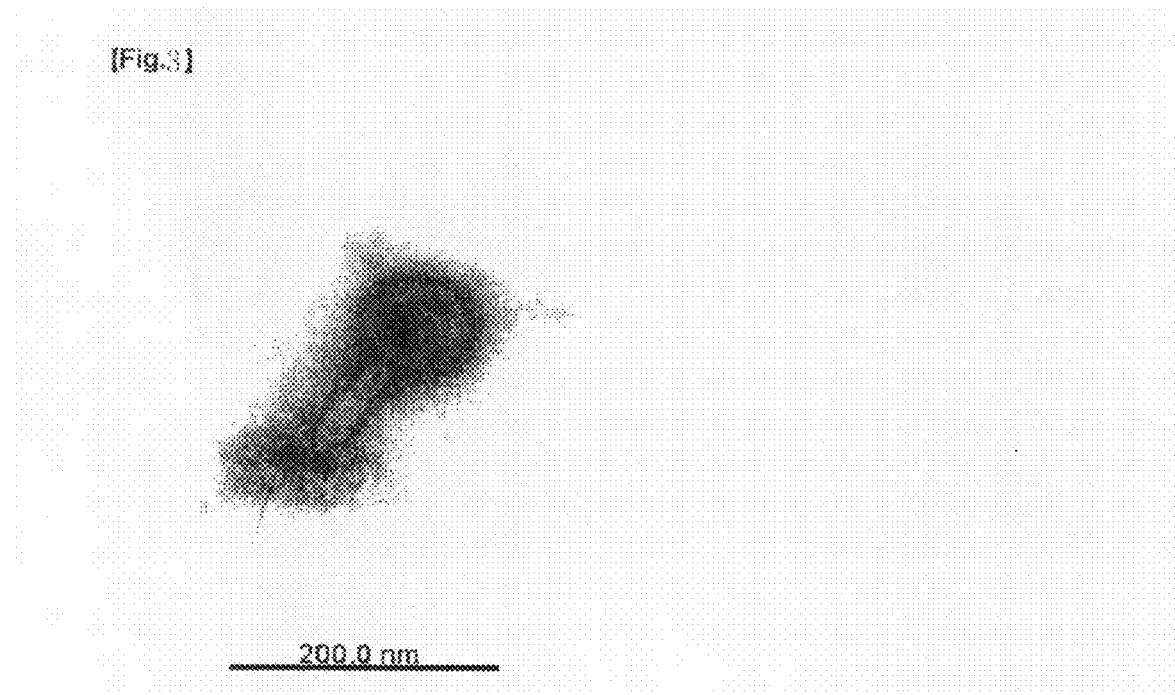
[Fig.4]
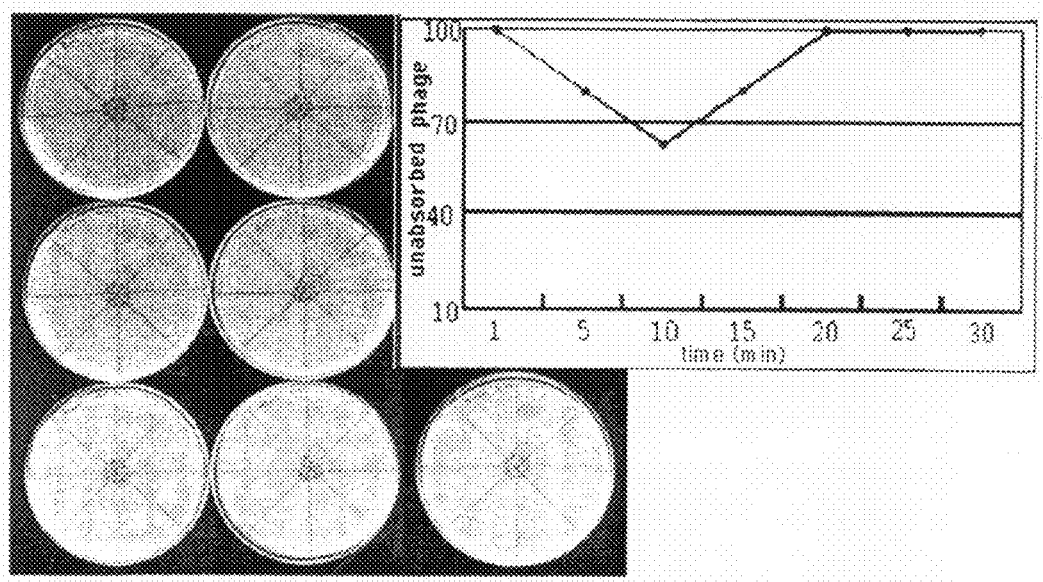

[Fig.5]
(A)
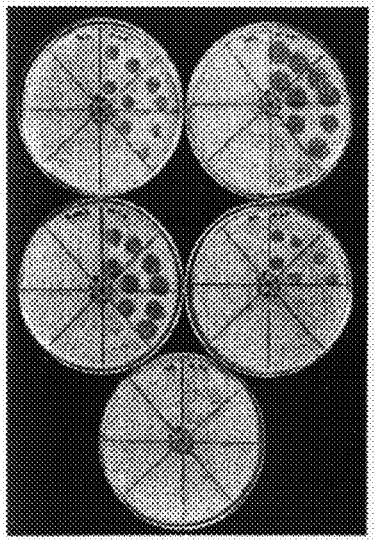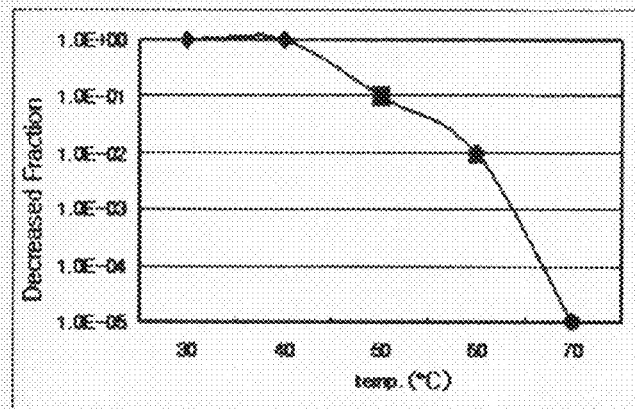
(B)
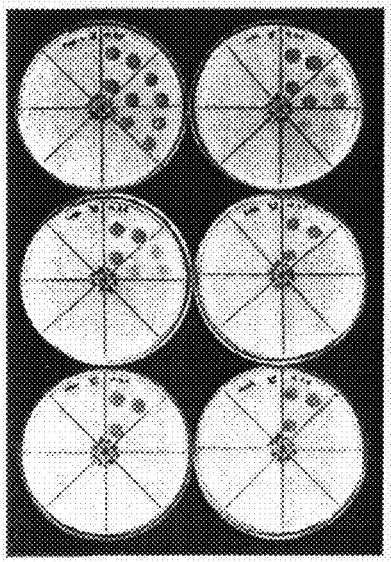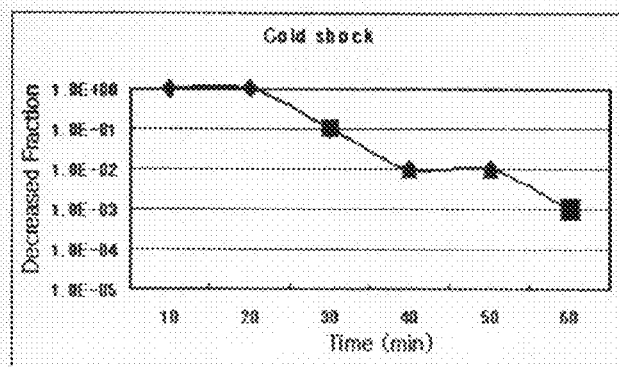

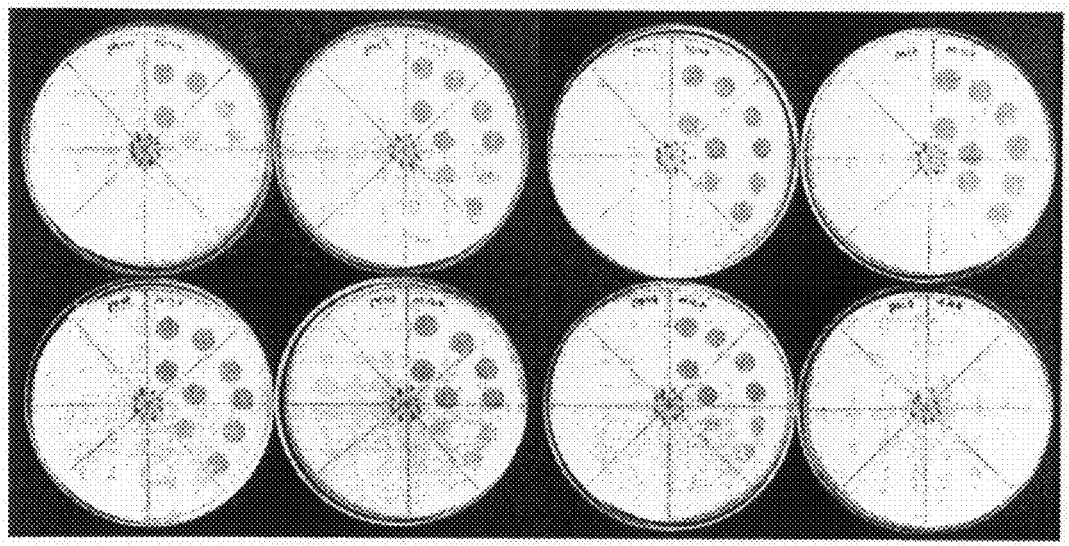
[Fig.6]

[Fig. 7]
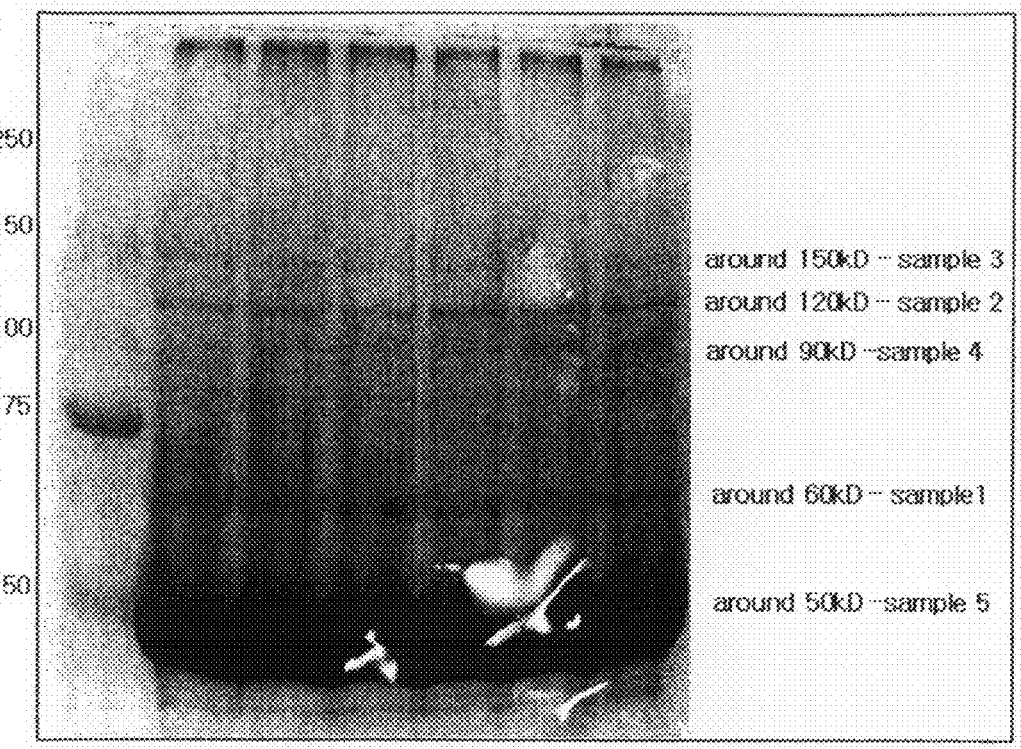
[Fig. 8]
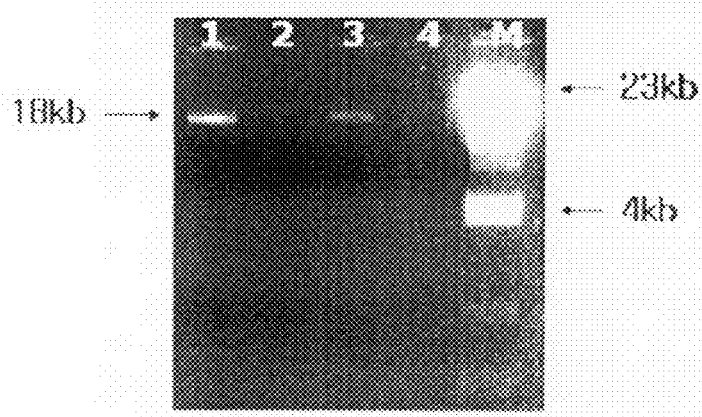

[Fig.9]
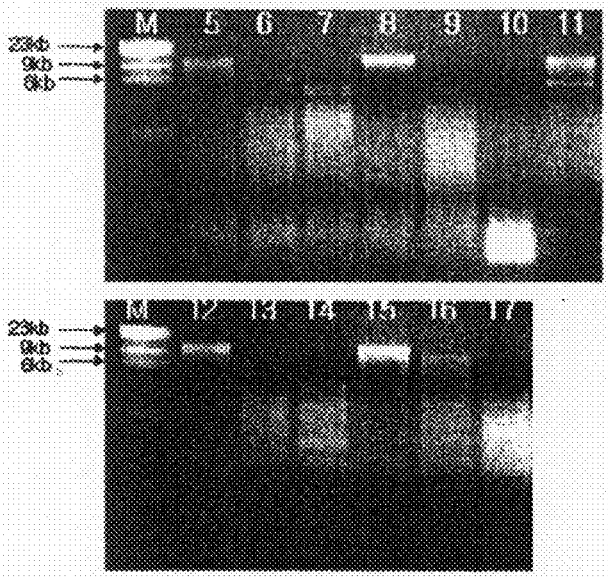
[Fig.10]
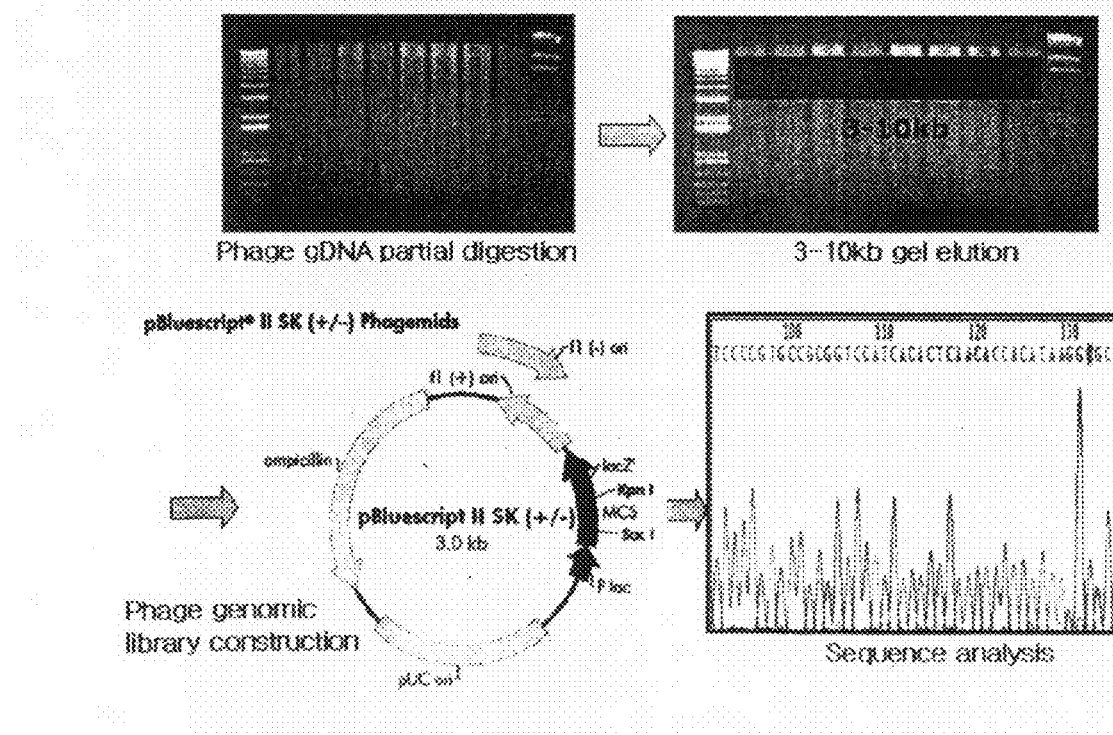

[Fig.11]
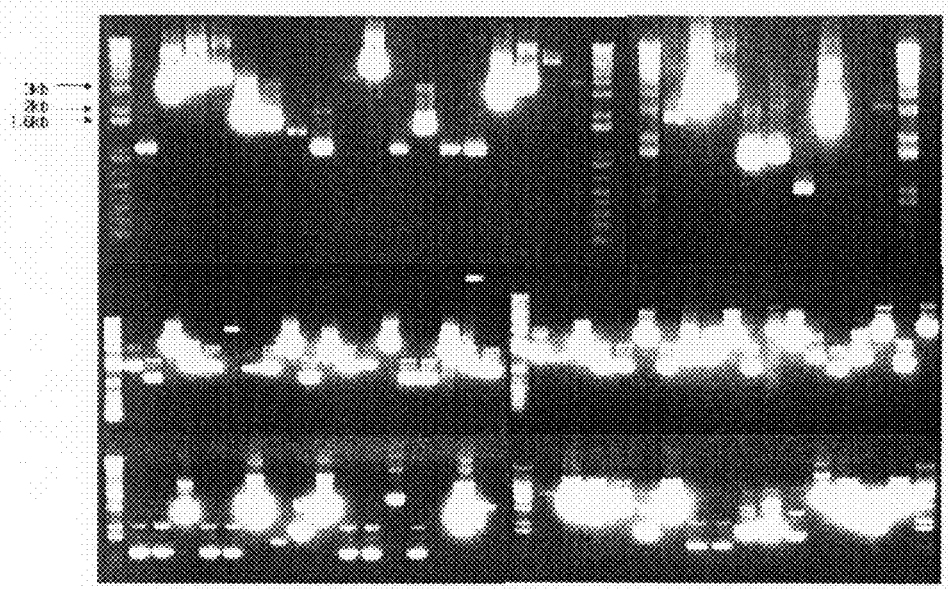
[Fig.12]
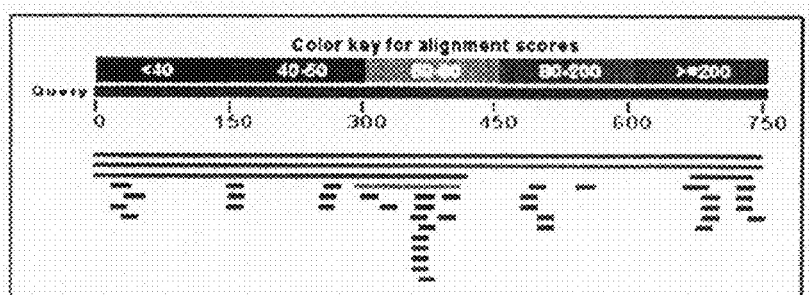

[Fig.13]
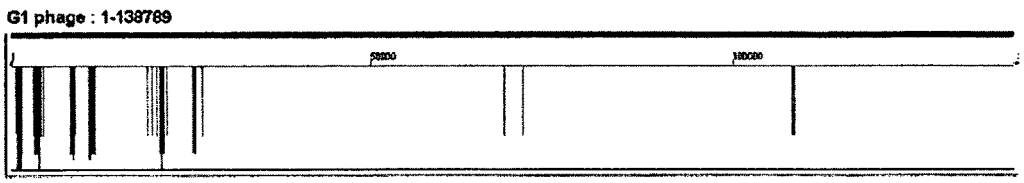

[Fig.14]
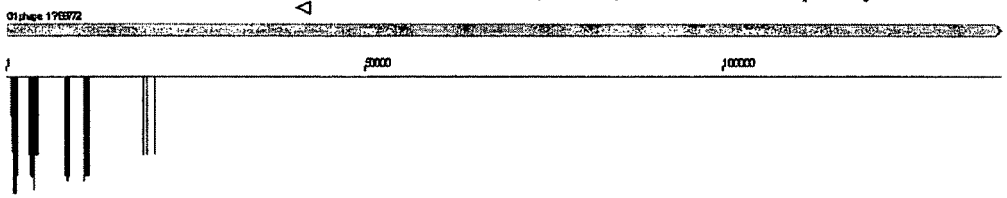
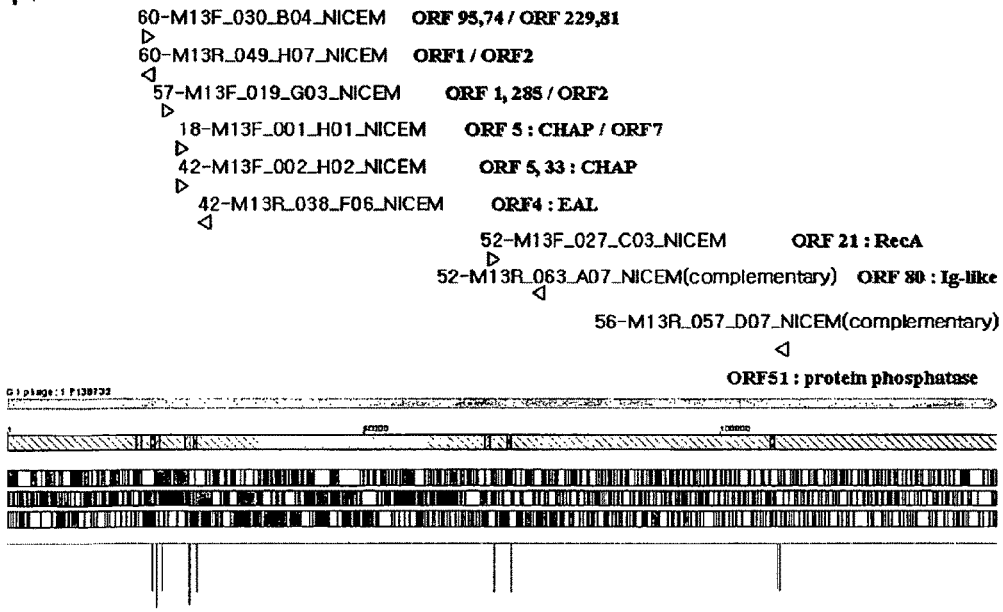

SEQUENCE LISTING

```
<160> NUMBER OF SEQ ID NOS: 47

<210> SEQ ID NO 1
<211> LENGTH: 776
<212> TYPE: DNA
<213> ORGANISM: Bacteriophage

<400> SEQUENCE: 1
tatgggtata cacaaattat atcaacaatc tgaccaatgg tattatggtc atagatgtca      60
acattgtgat tatttaaatg aaatgagtta taatgattac aaccctgata atcttgaaga     120
aagtgggaat atgttatgtg ttaaccctga aggtgtagat gaacaggcta aaacagtaca     180
```

```
gaatggtagt taccaatttg tttgtcaaaa atgcggtaaa ccactagata gatggtataa    240
tggtgagtgg cattgtaagt atcctgagcg tacaaaaggt aataaagggg tacgaggata    300
cctaataaca caaatgaacg ctgtatggat ttctgctgat gaattaaaag aaaaagaaat    360
gaatacagaa tctaagcaag cgttttacaa ttatattttg ggttatccat ttgaagatgt    420
ttaactgaga gttaatgaag aagacgtttt atggtaacaa atcacctatt gcagaaacac    480
aattaatgaa acgagataga tattctcata tagctaatgg tatagattgg ggaaatactc    540
attggataac tgttcatggt atgttaccta atggtaaggt agacttaata cgattattct    600
ctgttaaaag atgaccagac ctgatttagt gaagcagatt tagaaaaatc atttggggaa    660
atatctagta cgacctgata tataatgcga tacggagatc agaaacatgg tctaaactca    720
tatcatttga agataaagt atttgatgta cgtataatct tcctcttagt ctacag         776

<210> SEQ ID NO 2
<211> LENGTH: 1424
<212> TYPE: DNA
<213> ORGANISM: Bacteriophage

<400> SEQUENCE: 2
gaagctaaca aggcaattca aaaaagatgt agattcaggt aaggcaattg aactaggtga     60
tgtagctatt atagatacag cattaagtat tattctttca ggtaacgagt tccaaggaag    120
tattcgttta tgctaaaaaa agacttgaag aaaaagaaag aattagaaaa gaagaagaag    180
agaaacttaa taacttataa aagggaagaa ttatgagact atataaaatg aggtatcata    240
attgaaaaag aaaccacaag gcaatgagat aatcataacc ataataacgg ttatgatagc    300
aatatttgta gtcattatga ccatattttt taataaatac caagatgcta agaagataa     360 agatagatat cagagattag ttgagattta taaaaaagca gatgataatg atggagagac    420
taaaaagaaa tacgtaaaaa gattaaataa agctgaagaa gaacttaaaa agtaaagaa     480 agaaacaaat tataaagact ataataagaa gtcaaataaa gaaagacaaa aggaagataa    540
agaaactaga gagaaaatat atgatgtaac tggtgatgat gacttaatat tagtaaaaaa    600
taatattgag tttagtgata aggtagataa acctgaaata cttattagtg aagatggaat    660
tggtacgata actgtcccta caaacagtgg ttatgaaaaa caaacagtag gttctattat    720
tactagtgta ttaggttccc cgttcttatc aactgattca ccggtataga tagttaggta    780
tcatatagtt atgttatccc aaatacagta gatagtatag tagagataca aatacttcta    840
ctgataatgt actaaaggat aatccctatt ataacaaatc ccagttgaac ccaaccacac    900
cttcagatat attacctcct attgataatc ccgtcagttc ctatattacc tgaaaaccct    960
gtagacaata attcaggaaa tatagataat acgataatc caaaccctcc cacctccagg    1020
atataccaga tgaagatgga ggtagaggcc caggtggtgg aggtaatgtt gaacccccc    1080 caacggaaga accttcagat aacggtaata caggaggagg agattgggaa gaaaaacctg    1140
acccaggaga agagccatca gataatggta atacaggaga caatgaagga gaggtaactc    1200
ctgaacctga ccctacacct tctgagcctg acaacctaa tgaaaacct aatgagggta    1260 atggtaatga agaaaaacca tccgaaccat cagataatcc tgatgaaaat ggaggatggg    1320
aaactgagcc ttccgaacct gaaacacctt ctgagccgga cgataaggtg gacgaagagg    1380
ataaaaacga agatacaaca gaggataaac aacctacaga acaa                     1424

<210> SEQ ID NO 3
<211> LENGTH: 702
<212> TYPE: DNA
```

<213> ORGANISM: Bacteriophage

<400> SEQUENCE: 3

```
ctaaagaacc tgaaaaggtt actgaggaag atgctaaaga agcacaagag caaggtgaaa      60
aagttgaatc tgaagaggta acagaggaca ctgaagatga ggaagttgaa aaatcagcta     120
aagaatcaaa agaccctgta gaccaaaaag atactaaaac agaaaataaa gacaacgaga     180
aacgtaaaaa taaaaaagat aaaaaagaag attctgaatc tgatgatgaa gacaaagata     240
ctgacgatga taaagataag aaagaagata gaaggaaaa aacttctaaa tcaatttctg      300
atgaggatat cacaacagta tttaaatcta tcctaacatc ttttgaaaac ttaaataagg     360
gagaaagaaa actttgctac taaagacgat ttaagtgaag ttagtaaatc tattaatgaa     420
gttatcagca aaaatttctg aaatccaatc tgaaagatgt ttctaaatca gtagacactg     480
atgaagaaga agctgtagaa aaatcagtaa catctacaaa tggggagcaa gaaaaagtag     540
aaagttatgt ttctaaatca gtagacactg aagagcaagc tgaaactggt gaagcaaatc     600
agagatgctg agagtacaga gatacacatt aagatagtca gagaagacta gtcatgatct     660
ataagcacag ctaagaccta gagcttctaa acatgactta ca                        702
```

<210> SEQ ID NO 4
<211> LENGTH: 772
<212> TYPE: DNA
<213> ORGANISM: Bacteriophage

<400> SEQUENCE: 4

```
caacagccaa aaagatgaa aataagtaaa gggtgaatta aatggttaac tcaatgtttg       60
aggggactta gacctttgaa aaatcataaa ctatgaatat cttatcatcc tagtggtaat     120
cctaaacata tagacgtaag tgagatagat aacttaacat tagctgatta tggatggtca     180
cctgatgcag ttaaagctta tatgtttggt attgtagtac aaaaccctga tacaggacag     240
cccatgggtg atgagtttta taaccatata ttagaaagag cagtaggtaa agctgagaga     300
gcgctagata tttctatact acctgatact caacatgaga tgagagatta tcatgagaca     360
gagtttaata gttatatgtt tgtacatgct tacagaaaac ctatattaca ggtagagaac     420
ttacagctac aatttaatgg tagacctata tataaatacc ctgctaactg gtggaaagta     480
gagcatttag caggtcatgt tcaattgttc cctacagcac ttatgcaaac aggacaatca     540
atgtcatatg atgctgtatt caatggatac cctcaattag caggtgtata cccaccatca     600
ggagcaacct ttgcacctca atgatacga ctagaatacg tatcaggtat gcttccacgt      660
aaaaaagcag gtagaaataa accttgggag atgcctcctg agttagaaca gctagttata     720
aaatatgcat tgaaagaaat ataccaagta tggggtaact taatcattgg tg             772
```

<210> SEQ ID NO 5
<211> LENGTH: 784
<212> TYPE: DNA
<213> ORGANISM: Bacteriophage

<400> SEQUENCE: 5

```
aagaaataga taaattaaaa tatcaagata agcaagaaaa agaacaagta attaacaaag      60
ttattaaagg tgttaatgat acttgggaaa agaatataa ctttgaagaa ttagatttaa      120
gatttaaagt taaaattaaa ttacctaatg cacgagaaca aggtaacata tttgcgttac     180
gttctgctta cttaggtggt atggatatgt atcaaacaga ccaagtaatt agagcatacc     240
aaatgttagc tacattacaa gaagtaggta ttgaagttcc taaggaattc caagaccctg     300
```

-continued

| | |
|---|---|
| atgatatcta taacttatat cctttaactg ttatgtatga agattggtta ggattttttaa | 360 |
| actcctttcg ttactaatag tatagaaaca ttagataaag atatagaacg attgggtggt | 420 |
| atggaatcaa ttgttaaaca acctttatct agaaatctat gggctattat gaaagagttt | 480 |
| aatgttttgc ctactgagca aagatttaag gatttagacg attatcaaat agagtttatt | 540 |
| attggtaata tgaataggga tgtttatgaa cataataaac aacttaaaca agctcaaaaa | 600 |
| ggtggaaaat tcgacagtca atttgaagat gatgatagta gttggtggaa tgaatctcat | 660 |
| gaagactttg acccggtacc tgatttctta gatgccgatg acttagcaca acagatggaa | 720 |
| gctaaattat ctgatagaga taaggaagaa agagctaaga gaaatgatgc ggagttaaat | 780 |
| gatg | 784 |

<210> SEQ ID NO 6
<211> LENGTH: 761
<212> TYPE: DNA
<213> ORGANISM: Bacteriophage

<400> SEQUENCE: 6

| | |
|---|---|
| gaaggactca ctacacaaca tcttgctatg atggaataca ttagaagaaa acaagaagaa | 60 |
| ttagatgatg aagtaggaaa tggtaaaact agtgaagatg atgctactat atcacaagag | 120 |
| agcgttaata aagcactaga agacctagat gatgactggt atatgtaaag ggtggtaggt | 180 |
| gatactacca tccttatttt tttaaaatgg atggtgaata atgatggcaa tgaatgacga | 240 |
| ttatagattg gtcttatccg gtgatagttc ggatttagag aatagtctga aggcaataga | 300 |
| actttatatg gattccctag aatctaaaaa tattgatgcc cctttagaca atttcttaaa | 360 |
| gaaattaaaa gtaattgcta aagaagttaa aaatgtacag aactcaatgg ataaacaaga | 420 |
| aggtaaatct gtcatatctt ctaaagatat ggatgaatct attaaatcca ctcaatctgc | 480 |
| tacaaagaat ataaatgaat taagaaaagc cttagatgac cttcaaaaag aaaatatatc | 540 |
| taaaggtatt gcacctgacc ctgaagttga aaaagcatat gctaagatgg gtaaagttgt | 600 |
| agatgaaact caagaaaaac ttgagaaaat gtcttcacaa aaaataggct cagacgctag | 660 |
| tatacaaaat agaattaagg aaatgaaaac cttaaatcaa gtaacagaag atataataag | 720 |
| ataagtaaag attctagtgc tactaaagac tatactaaac g | 761 |

<210> SEQ ID NO 7
<211> LENGTH: 1472
<212> TYPE: DNA
<213> ORGANISM: Bacteriophage

<400> SEQUENCE: 7

| | |
|---|---|
| taaatagtac tgacatgttg aaaatggcta cttcatatga agcatctgta ggacataaaa | 60 |
| gtgatgagga tacaatggca ggaactaaac aacttgctat tggaggacgt tctttaggta | 120 |
| ttaaagacca agaagcttat caagagtcta tgggtcagat aatgcatact ggtggagtaa | 180 |
| attccgataa catgaaggag atgcaagatg cattcctagg cgggattaaa caatcaggta | 240 |
| tggttggtcg tcaagatgaa caacttaaag cattaggttc tatagctgaa caatcaggag | 300 |
| aaggaagaac tttaactaaa gaccaaatga gtaatcttac tgctatgcaa tctacttttg | 360 |
| cagagtcagg aagtaaagga ttacaaggtg aacaaggtgc caatgctatt aatagtatag | 420 |
| accaaggact taaaaatggt atgaatagtt cttatgctcg tatagcaatg ggatggggaa | 480 |
| cacagtacca aggtcttgaa ggtggatatg atttacaaaa acgtatggat gaaggtatat | 540 |
| ctaaccctga aaacttgaca gacatggctg atatggctac tcaaatgggt ggtagtgaaa | 600 |

| aagaacaaaa ataccctattc aatagaagta tgaaagaaat aggtgctaac gattaactat | 660 |
| ggagcgaatc tgatgagata cttaaagat gctcgaatcc ggaaaattat ctaaagaaga | 720 |
| gttagctaaa aaagctaaga aaatggaaaa agaaggtaaa aaagaaggag aagataacgc | 780 |
| cactgattat aaagaatcta aatcaggaaa aaatgaccaa aataaatcta agactgatga | 840 |
| taaggcagaa gatacttatg atatggctca accattaaga gatgctcata gtgctttagc | 900 |
| agggctacct gctcctatat atttagcaat aggagctatt ggagcattta cagcatcact | 960 |
| aattgcatct gcaagtcaat ttggggcagg tcatttaata ggtaaaggag ctaaaggact | 1020 |
| tagaaataaa tttggcagaa ataagggtgg tagctccgga ggtaacccta tggcaggagg | 1080 |
| aatgcctact ggaggaggtt cacctaaagg cggaggctct cctaaaggtg gcggtactcg | 1140 |
| ttctactgga ggtaaaatac ttgatagtgc taaaggatta ggaggattcc tagtcggtgg | 1200 |
| agcaggatgg aaaggtatgt ttggtggaga atctaaaggt aaaggattta acaaacatc | 1260 |
| taaagaagcc tggtcaggta ctagaaaagt atttaacaga gacaatggta gaaaagccat | 1320 |
| ggataaatct aaagatatag ctaaaggtac tggtagcggt cttaaagata tttataatga | 1380 |
| tagtatattt ggaaaagaaa gaagacaaat ctaggagata aagctaaagg ttttggtgga | 1440 |
| aagctaaagg tctctatggt aaatttgctg at | 1472 |

<210> SEQ ID NO 8
<211> LENGTH: 763
<212> TYPE: DNA
<213> ORGANISM: Bacteriophage

<400> SEQUENCE: 8

| taaccgacat tacaagtatc aatgtacttg gtatgcttat aatagaagag gtcaattagg | 60 |
| cattcctgtg cctttatggg gggatgccgc cgactggatt ggcggtgcta aaagtgcagg | 120 |
| ttatggtgta ggtagaacac ctaaacaagg agcttgtgtc atatggcaaa gaggagttca | 180 |
| aggcggtagt gctcaatatg gtcacgtagc ttttgttgag aaagtttag atggaggtaa | 240 |
| aaaaatattt atctctgaac ataactacgc tactcctaat ggatatggta ctagaacaat | 300 |
| agatatgagt tcagctatag gtaagaatgc tcaattcatt tacgataaga ataaaggag | 360 |
| gatagtctat ggcaacagat aaagaagcta agatgttat tgataaattt atagataatg | 420 |
| tatttaattt tgatgtactt acaaaagaaa gaataaaaga aaaagatgaa gaattaaaa | 480 |
| aaataactac agatgatatg tatgaaaaag ttgtttatat acgacccttat gttggagtga | 540 |
| tacaaagcct taaccctcaa catgtacaat atgaatcatt tctaataat ggttacgata | 600 |
| tagaagcaga attaagtttt aggaaagtaa gttatttagt tgataaaggg tctatacctta | 660 |
| cagattcttt atccacttta acagttcatt tagtagaaaa aaaccaggag ttattaatag | 720 |
| attactttga tgagatacaa gatgtgttgt atggggaata tat | 763 |

<210> SEQ ID NO 9
<211> LENGTH: 696
<212> TYPE: DNA
<213> ORGANISM: Bacteriophage

<400> SEQUENCE: 9

| gatgaagagg tgtatattta atggtagtaa gatttccaat cttccatggg gagaagtcta | 60 |
| aaaagagtag attcagatga cttaaatgta aaagggttag ttttagctac agttagtaaa | 120 |
| attaattata gtatcaatc agtagaagtt aaagttaata acttgacttt aggaagccgt | 180 |
| ataggtgatg atggtagctt agctgtacct tatcctaaat ctttcatagg tagaacacct | 240 |

| | |
|---|---|
| gagggaagtg tatttggtac aaaaccactt attactgaag gttctgtagt attaatagggg | 300 |
| ttcctaaatg atgatataaa tagtcctata atcttgagtg tttacggtga taatgaacaa | 360 |
| aataaaatga ttaatacgaa tcctttagat ggaggtaagt ttgatacaga aagtgtttac | 420 |
| aaatacagta gttcactata tgaaatttta ccatctttaa attataaata tgatgatgga | 480 |
| gaaggaacaa gtattagaac ttataatggt aaatcattct tctctatgac atcaggtgaa | 540 |
| gaagagaaac cacaggcaac agatttttat actggaactg agtatcaaga tttatttact | 600 |
| tcctattacg gtaataaaac attgattgaa cctagaatac aaaaggctcc taatatgtta | 660 |
| ttcaaacatc aaggagtttt ttatgatgat ggtacg | 696 |

<210> SEQ ID NO 10
<211> LENGTH: 755
<212> TYPE: DNA
<213> ORGANISM: Bacteriophage

<400> SEQUENCE: 10

| | |
|---|---|
| aagaggtcat cgagaataaa aactatgtac cacctaaaat caataatggt gatgaggatt | 60 |
| cccaacaaaa tactgtacct aaagaacaat atgatagttt aaaagaagag ctagaactta | 120 |
| tgagacagca acaagaagct atgatgaaaa tgcttcagca actcttaggt caaaaggggt | 180 |
| aataataaat ggcattaaat tttactacaa taacagaaaa caatgttatt agagacctga | 240 |
| ctgttcaggt caataacatt ggagaagagt taacaaaaga aagaaatata tttgacatta | 300 |
| cggatgattt agtttataat tttaataagt cacaaaaagt taaattaaca gatgataaag | 360 |
| gtttatctaa atcttatggt aatataactg taattaggga tataaaagaa ccaggttact | 420 |
| attatataaa tgcaagaaca ttagctacac tattagataa acctgatata gaatccatag | 480 |
| atgtttttact tcatgtatta cctttagatt catctagtag agtaatacag catttatata | 540 |
| cgttgtctac taacaataat caaattaaga cattatatag atttgtttca ggtagctcta | 600 |
| gttcagaatg gcagtttata actggattac ctagtaataa aaatgctgtt atttcaggaa | 660 |
| ctaatatttt agatatagct tcaccaggtg tttactttgt tatgggaatg acaggaggaa | 720 |
| tgcctagtgg tgtagattca ggttttctag atttg | 755 |

<210> SEQ ID NO 11
<211> LENGTH: 665
<212> TYPE: DNA
<213> ORGANISM: Bacteriophage

<400> SEQUENCE: 11

| | |
|---|---|
| gttaaactta aaaaaacata atgcacattt ccaaaaagtt gttagagaaa agaatgaaaa | 60 |
| gaaatatgat aaatatcaag atatgagaga ctttttagat tcagtgactg ttatgatagt | 120 |
| tgatgaagca catcactcta atcagattc gtggtataat aatctaatga catgtgaaaa | 180 |
| agctttgtat aggattgcat taacgggttc tatagataaa aaagatgaat tactatggat | 240 |
| gagattgcag gctctatttg gtaatgttat tgcacgaact actaataagt ttttaattga | 300 |
| tgaaggtcat tctgctagac aacaataaa tattataccc gtagctaatc ctaatgacat | 360 |
| agatagaatt gatgattaca gggaagctta tgataaaggt ataacaaata atgatttag | 420 |
| aaataaactt attgcaaaac taacagaaaa gtggtataat caagataaag ggacattgat | 480 |
| tattgtaaac ttcatcgaac atggagatac aatatcagaa atgttaaatg atttagatgt | 540 |
| agagcactac ttcttacatg gagaaataga ctctgaaacc cgtagagaaa aattaaatga | 600 |
| tatgagaagt ggtaagctta agtaatgat agctacatca cttattgatg agggtgtaga | 660 |

<210> SEQ ID NO 12
<211> LENGTH: 789
<212> TYPE: DNA
<213> ORGANISM: Bacteriophage

<400> SEQUENCE: 12

```
attcaaatcc ttttaatgac tttgatgtaa acagtgttga tgattcacaa gtacttttg      60
agacacaacc tcaaaacaca caacaagcac ctgaaccaca caaactact caggagcctc     120
caaaacaaaa acaaacacaa agtattgacg atgtattagg tggtctagac ttagataacc    180
tataagatat agagtgcctt agagcactct tttatttgag atataattac taggaggata    240
ttaaatggca agagcaaaaa aaggtaaaga agtagattta acagatttaa atacaattga    300
tttaggtaaa gaattaggat taacattatt atcagataca aatagagcag atattaagaa    360
tgttatacct acaatggtac ctcagtatga ctatatttta ggtggaggta taccgttagg    420
tagattaaca gaggtttatg gtttaactgg tagtggtaaa tcaacatttg cagttcattt    480
gtctaggatt gcaacacaat taggtgttat taccatttgg attgatattg aaggaacagc    540
agacaataat cgtatggaac aacttggagt agatgtttca aaattattct ctattcaatc    600
aggagaaggt agacttaaaa atacagtaga attatctgta gaggctgtag gtaaagaatt    660
agagtactgg attgacacat ttaatgaaaa gatacctgga gtaccattg tgtttatttg    720
ggactcacta gagctacacg aactcagaaa gagattgacg gcggtattga tgagaaacaa    780
atgggtctt                                                           789
```

<210> SEQ ID NO 13
<211> LENGTH: 685
<212> TYPE: DNA
<213> ORGANISM: Bacteriophage

<400> SEQUENCE: 13

```
tcctaaggaa gacggagcag acgtatcagc agaataatat agataaagga tggtaaattt     60
ggctaagtta aatttataca aaggtaatga gttactaaac agcgtagaga aaacagaagg    120
aaaatcaaca atcacgattg agaatttaga tgctaacaca gattaccta aaggtacttt     180
taaagtatca ttctcaaatg attcaggaga atcagagaag gtcgatgtcc ctcagtttaa    240
gacaaaagca attaaagtta tttcagttac ccttgacgtt gatagtttag accttacagt    300
tggagatact caccaactat caacaactat cacgcctagt gaagcatcta acaaaaatgt    360
gtcatttgaa tcagacaaat caggtgttgc tagtgtaaca tcagaaggat taattgaagc    420
agttagtgca ggaacagcta atattactgt aactactgag gatggtagtc atactgtatat   480
tgttgcggta acagttaagg aacctattcc tgaagcacct acagatgtaa cagttgaacc    540
tggtgaaaat agcgcagata ttactgcata ggaggacaat aaagaatgga aaagacatta    600
aaagtttata gtaatggtga agttgtaggc tctcaagtag ctaataacga tggagctact    660
acagtatcta ttacaggctt agaag                                          685
```

<210> SEQ ID NO 14
<211> LENGTH: 700
<212> TYPE: DNA
<213> ORGANISM: Bacteriophage

<400> SEQUENCE: 14

```
tctcacccat ctacatctac aaaagtattc cattccatat ctatacaaga acgttcacta     60
```

```
ctttctataa aggcatttaa atcggcatat aattgaacaa aaaaagacat atcatagttc      120
caatacttag gttcatttct tcctaatttt ttattcattt ttttatactt tctatttctc      180
tttaacccaa aaacttcttt ttcaaaatca tttaatttta aacctttaaa atattttttc      240
ttcatatcta atcctccaat ttaataagtg gtaaatctat atctaaaat acagaaccta      300 cgtcacatag cagtatatca ttatgttctt ctacttcacc actactagta ggtgtatgac      360
cacatacata tataaatcca tcttttctag gttggaagtc tctagaccat attaactggt      420
ctactgtttg ctcttctata ggtttccaac taactccccc tgaatgggaa aatatatact      480
taccttcttt ataatacctt ctacaattaa ccataaatat tttaaatttt ctataatctt      540
cagattcttt aagtttcttt agttcacttt taataaaatc ataatgattt cttaaattat      600 cttctcacact tttatatttt aaagttacag tactaacacc gtaagagtta agtgtttcta      660
tacaatacct tgataaccat tcaatatcat agatacttaa                            700

<210> SEQ ID NO 15
<211> LENGTH: 789
<212> TYPE: DNA
<213> ORGANISM: Bacteriophage

<400> SEQUENCE: 15
gaatggtacc cgatgaacca gctgttggcg ttgcacaaat aatacccatc gcagcattga       60
cttcatttgt tgcaatggca cctttgactg catcaatcat ttcatatcca gacaaagcat      120
gatgtgtttc attataatca cgtagtttag cagcgtcatg accagtgtag cccgttacac      180
tttcaacgcc atcacctgtc gtccctttga ttactgcgtc tcgcatgaca tctaaatttt      240
gtttcatttg cgctcgcact tcatcacgtg atttaccgct taattccatt tcttctttaa      300
ccatgatatc cgcaaatgac atattatttt ctacggcata atctatagtc tctctaattg      360
aatcaaacat gtttattccc cctctaattt atataggaaa cgtttacgtc actgtatttc      420
tctttaattg tatttaatat cgattctgag attgctttat ttaatggtat tacaaccaag      480
catttatctt catctatctt aataaaattca tctttacagt ctaatttcat atcgttgata      540
tcattaatga aatgatttac ttgtgcttta gtcatatttc cgtcaacaac taaaattggt      600
aatccatgat ttaaatctac ttctagtcca tttatatgaa tacctttaat tttaattgta      660
ccaccaccga ttgaataccg atatttcata tagcaccatc atacgagatg attatatagc      720
acagtttgga tgttgacata ctatcgcttc tcttcgatga tatctatttt aataccatca      780
tcagctgca                                                             789

<210> SEQ ID NO 16
<211> LENGTH: 710
<212> TYPE: DNA
<213> ORGANISM: Bacteriophage

<400> SEQUENCE: 16
gctaaatgtc acgatacatg cgtgacgacc ccaatcagtg catttgtacc atatagtgta       60
ctggatatgc gctataaatc aatttgcgtc aatggctcaa tacaaactgc aaatgctttg      120
acggtccacc aatgttttaat tttcggaata aaataaggtt aacaaatgag ctacctgtac      180
atgttagtgc tccaatagcc ataggaacac ctgtcagtcc taataaactt gttaatacca      240
ttgaacttag cggtgtcata cctgtaacag gaatcactag tcctaaaatg accgctaatg      300
catatggatt gttatcacct accgcagtaa cagcactacc tatttgtttt aatgttgcta      360
gcacaccagg tgtaatgatt gatgcaagtc cgaaagcaat tgctggtgca aataagatca      420
```

```
ccacaattaa gtccaagcct tctggaactt tcttttcaat ccatttaatt aaaaaagcta        480
cgccataagc tgcaatgaat gctggtaata atttaaagtc atgtaatact aaaccaacaa        540
tgaccgcaaa tactggtgca acgcctaagt ttaagcacgt tagaataccct actgcgatac      600 cgcttaaact tcctgctaaa tccccaatat cttgtagaaa tttaatatca aatacgccac        660
caatggcata acttaagaat gcttgtggta gaaatgtcgc acaagctgca                   710
```

<210> SEQ ID NO 17
<211> LENGTH: 762
<212> TYPE: DNA
<213> ORGANISM: Bacteriophage

<400> SEQUENCE: 17

```
gagacaaagc taaagaatta aatatcgaac cattggcagt gcttgatggc tttggaagtc         60
atggtgtaga tcctttctat tatgggtatc gcaccagttg gcgctgttga aaaggctttg       120
aaacgtagta aaaagaatt aagcgatatt gatgtatttg aattaaatga agcatttgca        180
gcacaatcat tagctgtaga tcgcgaatta aaattacctc ctgaaaaggt gaatgttaaa       240
ggtggcgcta ttgcattagg acaccctatt ggtgcatctg gtgctagagt tttagtgaca       300
ttattgcatc aactgaatga tgaagtcgaa actggtttaa catcattgtg tattggtggc       360
ggtcaagcta tcgctgcagt tgtatcaaag tataaataat aagaaaacag gttatcacaa       420
cagtattaat tacatgttgg cataacctgt ttttatttgt ttatggattt attgggtaat       480
attagtcatt tgatggttta attgcaaatg ctctaacagg gaacccaggt gcatcttttg       540
gtttagggct gatagcgtaa atgatggcgc cacgagttgg taattgatct aaattagtta       600
ataactcgac ttggtatttta tcctgaccaa gaatataacg ttcgccaact aaatcaccat      660 ttttttacaac gtccacagat gcatcggtat cgaatgtttc atgaccaaca gcttcaacac    720
ggcgttcttc aattaagtac ttcaaagcat ctaatcccca ac                           762
```

<210> SEQ ID NO 18
<211> LENGTH: 673
<212> TYPE: DNA
<213> ORGANISM: Bacteriophage

<400> SEQUENCE: 18

```
acgttctact aaatgcatca tattaacagg tgataataca agatgtttct gaaatggaat         60
aagccctgtc gctgcaatga atacgcctaa aaatccaggg atgtaatgga tactttgcgg       120
tagtactaat gatagaaatg ataaaaatga atcacaaag gctacggtcg caaaagcttg       180
acatgtacgc ttatcgccat aatctaatcc tgtacgtata tgtaataaat actgtaatcc      240
gatacttaag tacataattg ccacgcataa gaagaatggg aagaatgtct tttcaaagtc      300
cggatatagg ctgttagata ggaagaccat gataaacata ttaaacatca taaacgaaac      360
gtctttgaat gtaacttgac caaatcgatt tgtaaaaaat gtttgatgag accacattaa      420
ccataagaac aaactcatga cgatgtattt gaaaaacaaa tcagctgaaa tggaaccatt      480
ttgtgttgtt aaaatcacat gtgcaatttt ttgaatggca tagacgaaaa ttaaatcaaa      540
gaacaactca tggaatcctg cacgcttttc agctaaatgt tttggtgtta atgcattaac      600
cataaaattt taactccttt aagatgtgta attaatttac taagtatact atttattttt      660
tctagtgaat agg                                                            673
```

<210> SEQ ID NO 19
<211> LENGTH: 766
<212> TYPE: DNA

<213> ORGANISM: Bacteriophage

<400> SEQUENCE: 19

```
cacatttagt acaaaataac gacattatcg ttattacatg caattatcgt ttaggcgcac      60
taggatattt agactggtca tattttaata aagattttca ttccaataac ggactttcag     120
atcaaatcaa tgtcataaaa tgggtgcatc aatttattga atccttcggt ggcgacgcta     180
ataacattac tttaatgggt cagtctgcag gcagtatgag cattttgact ttacttaaaa     240
tacctgacat tgagccatac ttccataaag tcgttctgct aagtggcgca ctacgattag     300
acacccttga gagtgcacgc aataaagcac aacatttcca aaaaatgatg ctcgattatt     360
tagatacaga tgatgttaca tcattatcga cagatgatat tcttatgctg atggcgaagc     420
taaaacaatc tcgaggacct tctaaagggc ttgatttaat atatgcgcct attaaaacag     480
attatataca aaataattat ccaacaacga aaccaatttt tgcatgtaat acaaaagatg     540
aaggcgatat ttatattact agtgaacaga aaaaattatc gccgcaacgc ttatcgaca     600
ttatggaatt aaatgatatt cctttaaaat acgaagatgt tcagacggcg aagcaacaat     660
ctttagcgat tacacattgt tatttcaaac agccgatgaa gcaatttta caacaactca     720
atatacaaga ttcaaacgca aaactatggc ttgctgaatt tgcatg                    766
```

<210> SEQ ID NO 20
<211> LENGTH: 654
<212> TYPE: DNA
<213> ORGANISM: Bacteriophage

<400> SEQUENCE: 20

```
aaaacaacga ttaatcctaa tgcgccaatg atggcactcg tatacgtgat agcttgaaca      60
gaaacatgtg tcatgaccaa gcctccaata atgccaccaa caccaatacc agcgtttaaa     120
ctagacatgt tccaactcat tacttggctt gtgtcgcctt caacatgttg aatcacaccg     180
ctttgcactg ctggattagt actccattgc atgatattcc aaataaatag tcctgctaac     240
aatagacctg aaccaggtaa gattaaaattc ataagtaaca tcatgacgat aaaaatagaa     300
accgaaatca ttaaccaacg cttacttgta attttatcgg agaatatacc acctaatgat     360
gttccaataa cgccagcgat tccatttact agaagtgcta atgaaacgaa tgacatatca     420
tgaccattag ataaaataag tggatttata agacgaatg tcactgagtt tgcaatcaat     480
actaaaaacg taataattaa atattttgct acttcagcag gtcttaatat tttcgaagta     540
acatgatttt catgagatgg tgcctcatga ttcacagggc ctcgttgtat ttcctgatcc     600
ttcggtaaat agatcaccat caagaagcca acaataatac tcacaataat taag          654
```

<210> SEQ ID NO 21
<211> LENGTH: 764
<212> TYPE: DNA
<213> ORGANISM: Bacteriophage

<400> SEQUENCE: 21

```
tctaaactta tagacatctt gtttaacctc tttgttagta atccattgac tttgtccatt      60
atcattcgct tgtttaccat ctaaacttgc agatactttc actgtaattt gtggcagttg     120
ctttgctttt gcttttaaaaa agtcttggta taattgtgat gcacgttcat catcaacgca     180
ttcaacctca ataccgtgat cccgtaacgt atcatcacca tgtgtatcta acgaattgtc     240
ttttgttgcg taaactactt tagctatctt acaatcaatt attttgttaa cacagggtgg     300
tgttgaacca aaatgactac atggctctaa cgtaatataa atcgtcgcac cttcagcatt     360
```

```
ttgttgtgcc atatcaagtg cttgaacctc cgcatgcttg tcaccttttc tcaagtgtgc      420
accaataccg acaatcctac cttctttaac tacaactgcg ccaacgggtg gattaacacc      480
tgtttgacct tgtaccatat ttgcaagttg aatcgcataa tccataaatt gactcaaatg      540
atcacctcta taaacaaaaa tcctcacatc atgaattaag atgcaaggag aaaaatttat      600
cgttaaataa gcctatttgt acacattttt acaaatacgc tacattatct ttgtcgataa      660
ttaacattct ttctcccatc cagactttaa ctgtcggctc tagaatctca ctagatcagc      720
cactaatatg aaacatatta gcaggtcgca ggctttattt actg                      764

<210> SEQ ID NO 22
<211> LENGTH: 367
<212> TYPE: DNA
<213> ORGANISM: Bacteriophage

<400> SEQUENCE: 22
ctgatactgt gaattttttg gatctttgta cggtgaaaaa ttgtggcgcc ctcgggtgga       60
agtaggaatc tttggtcgga gacgtcggcc acagtaggaa ttcgttggtg agtgcggtcg      120
aatgtcaagt ttacagacta caatcatgac tataggaat agaaaaaatt aaaaaatttg      180
ttcatttaat acttcgatgc ctgatgagcg ctaattcatt ggaaacttac aatgctgata      240
atgatcgaaa ataagaccg atgaatcaat gtattgtgtt tagtttcctg aagattgagg      300
ggaaggtgca aagatactt tgattcgaca tgatgttaat gaagacaata ttgatgtagc      360
atttgtt                                                                367

<210> SEQ ID NO 23
<211> LENGTH: 767
<212> TYPE: DNA
<213> ORGANISM: Bacteriophage

<400> SEQUENCE: 23
ttttactcat gcatgcctat tttcaagtga gtctgagaca taaatcaatg ttctacgctt       60
tacaaagtta tattggcagt ggggccccaa tacagagaaa ttggaatccc aatttcaaca      120
aacaatgcga gttggggcgg tacaacgaaa tgaattttgt gaaatatca tttctgtccc       180 attccctgat gaatatgtgt atttaaaaag gacgttacct acattaaagt aagtcacgtc      240
cgtatgctta tgattactg tcactgtttt caattcgatt gatagtaaca tttagtccaa       300
atattttttc taaaaaatgt ttatagttat ctttagtgac agctaacttt tctgagatgc      360
catcctttgc ttttgtcaaa gttaaatgat tttcagacat tgtagcacgg ccaaacgatt      420
gtggcattgt aattaataaa tgctgtacaa atattgaatc tggatgcgtt tgattatatt      480
caatattttt atcaaaatct gcaatacatt tagctttaaa ttcagcttca tattttgtat      540
gccaatgatc atttttcgaat ttttgaacat agaaaatatc cttgtcttcg ttgttaaaga      600
tagcacgaaa cgtaccactg atgtcagtaa tcggttgtgt atgctctgac gaagtaatag      660
gaatggcgtg tagaggtaag tctccaaagc caacatcagt tacatagaat acatcattta      720
tagaaacaac aagtgaagca tgtgaaccgt tcagactgcg accgcca                    767

<210> SEQ ID NO 24
<211> LENGTH: 698
<212> TYPE: DNA
<213> ORGANISM: Bacteriophage

<400> SEQUENCE: 24
catgaaggaa atattaccca tcaatttcat aaatgctatt gcggcgaata ctgcatgtaa       60
```

```
tatagcaatc aataatggta aaccgaagtt gaaagtaatt tttaataata atcccttaag    120
catatctgta tgcgtaaagc ctatgcgttt taatattctg aagttactta gttcatcctc    180
agtttcatcc atttgtttaa tataaataat acatccagct gctactaaaa atgctaatcc    240
taaaaatgat gtaacaaata ttagaatacc gttagtagca tcgacctctt ttttcatgtc    300
atcatacgtg attactttgt ctccaaactg ttttgcaatt gcttgagctt tttccttttg    360
tgatgtttgt ttaatatcat acccataaaa agtatgaaca ttattttgtg ttttcaactg    420
ctgatacttt tcaggactta cttcgacgac aggtgagttg aagcttagat ttaaaggata    480
aaccttacct ttgtcttctt gtgtaacacg gaaagtttca ttcttagttc cttttactac    540
taaatctttg tttaaaagga tattaatcac gttaggcagc gactttgtat ttgtaatgat    600
ggcattgtta ccagttaact ttgtatttgc acttaaaata gaattcgtgc gacctgaatc    660
actaccattt tccaaagtaa taacctgatc tttaacat                           698

<210> SEQ ID NO 25
<211> LENGTH: 774
<212> TYPE: DNA
<213> ORGANISM: Bacteriophage

<400> SEQUENCE: 25
agggttatac gatatcacac agcaagcgaa tgctaaggca gctggtattc gtattgctgt     60
tgccgaaaag gcgggaaagt tgtcggcatg tatttattag aaaacagagg gagttcacat    120
tccacctcgt tacaaaatgt ttttgctctc gtgcgagaat caaaactgtc tatgaaaatc    180
gaattcgatt gattgagtgc atactctttt taattattaa catatttccg ttttcccaat    240
ggaggagacc tttactgaga tacatctttt gctaattctg tcaaaaccaa tagattatgg    300
tatgcaagtg gcttacctgc gagcgatcag tattgaaaac cactggaaaa catctatctc    360
atccttcgat ttctgttttc gaccctatta cagttgtaga tacacaggtg tgctatggat    420
caaagatgaa ggcttgattg ttattttaaa tatgggccag cacgacagtt ccatcttttc    480
tatatcgaac gaactctaat gttcccattt attgttacaa tgcctcgtaa tccccctcta    540
ttaagagctg aagattctta ttactaacaa ggcctaaata gatagatgct acggaacact    600
tctccaaaca acaaaattat tatctttttt tcttcccgga aatgttttcc atgctgactt    660
cacccccgga cgactgtcag ctacaccgat tagtgcgacc atacgggtca tcttgcttct    720
tgctacatga aaaagaaaca atcctacaaa taaagattat gtctaggtgc acgt          774

<210> SEQ ID NO 26
<211> LENGTH: 703
<212> TYPE: DNA
<213> ORGANISM: Bacteriophage

<400> SEQUENCE: 26
gatttcccta atgcagcaaa agatgaacat ggtcgtctac ttgtagccgc agcaatcggt     60
atttcaaaag acactgatat tcgtgctcaa aaattagtcg aagcaggtgt ggatgtctta    120
gttatcgata cagcacatgg tcactctaaa ggtgttatcg atcaagtgaa acatattaag    180
aagacttacc cagaaatcac attagttgca ggtaacgtag caactgcaga agcaacaaag    240
gatttatttg aagcgggtgc agatattgtt aaagttggta ttggcccagg ttcaatttgt    300
acgacacgtg ttgtagcagg tgttggtgta ccacaaatta cagcaattta tgattgtgca    360
actgaagcgc gcaaacatgg taagctatc attgctgatg gtggtattaa attctcagga    420
gatatcatta agcattagc tgctggtgga catgcggtta tgttaggtag cttattagca    480
```

```
ggtactgaag aaagtccagg cgcaacagaa attttccaag gtagacaata taaagtatac    540
cgcggtatgg gctctttagg tgcgatggaa aaaggttcaa acgaccgtta cttccaagaa    600
gacaaagcgc ctaagaaatt tgtacctgaa ggtatcgaag gacgtacagc atataaaggt    660
gctttacaag atacaattta ccaattaatg ggcggagtgc gtg                      703
```

```
<210> SEQ ID NO 27
<211> LENGTH: 19
<212> TYPE: PRT
<213> ORGANISM: Bacteriophage

<400> SEQUENCE: 27

Arg Ala Arg Ala Ala Ala Glu Asn Ile Ile Pro Asn Ser Thr Gly Ala
  1               5                  10                  15
Ala Lys Ala

<210> SEQ ID NO 28
<211> LENGTH: 17
<212> TYPE: PRT
<213> ORGANISM: Bacteriophage

<400> SEQUENCE: 28

Arg Ala Ala Ala Glu Asn Ile Ile Pro Asn Ser Thr Gly Ala Ala Lys
  1               5                  10                  15
Ala

<210> SEQ ID NO 29
<211> LENGTH: 18
<212> TYPE: PRT
<213> ORGANISM: Bacteriophage

<400> SEQUENCE: 29

Lys Leu Leu Asp Tyr Ala Glu Ala Gly Asp Asn Ile Gly Ala Leu Leu
  1               5                  10                  15
Arg Gly

<210> SEQ ID NO 30
<211> LENGTH: 14
<212> TYPE: PRT
<213> ORGANISM: Bacteriophage

<400> SEQUENCE: 30

Arg Ser Ile Gly Ser Asn Ile Ala Asp Ala Val Lys Lys Val
  1               5                  10

<210> SEQ ID NO 31
<211> LENGTH: 10
<212> TYPE: PRT
<213> ORGANISM: Bacteriophage

<400> SEQUENCE: 31

Arg Lys Ala Ser Leu Ser Gly Leu Arg Cys
  1               5                  10

<210> SEQ ID NO 32
<211> LENGTH: 17
<212> TYPE: PRT
<213> ORGANISM: Bacteriophage

<400> SEQUENCE: 32

Arg Ile Asn Glu Val Thr Gln Asp Tyr Leu Gln Val Arg Ile Asn Lys
  1               5                  10                  15
```

Leu

```
<210> SEQ ID NO 33
<211> LENGTH: 16
<212> TYPE: PRT
<213> ORGANISM: Bacteriophage

<400> SEQUENCE: 33

Lys Lys Ala Gly Leu Ala Val Gly Ala Ser Tyr Tyr His Phe Lys Thr
1               5                   10                  15

<210> SEQ ID NO 34
<211> LENGTH: 15
<212> TYPE: PRT
<213> ORGANISM: Bacteriophage

<400> SEQUENCE: 34

Lys Asp Leu Asn Val Val Asp His Val Leu Lys His Asp Arg Leu
1               5                   10                  15

<210> SEQ ID NO 35
<211> LENGTH: 14
<212> TYPE: PRT
<213> ORGANISM: Bacteriophage

<400> SEQUENCE: 35

Lys Thr Ile Lys Thr Glu Val Asp Pro Leu Met Thr Arg Ala
1               5                   10

<210> SEQ ID NO 36
<211> LENGTH: 15
<212> TYPE: PRT
<213> ORGANISM: Bacteriophage

<400> SEQUENCE: 36

Lys Thr Asn Thr Val Asn Ser Ser Lys Leu Asn Thr Pro Lys Asn
1               5                   10                  15

<210> SEQ ID NO 37
<211> LENGTH: 17
<212> TYPE: PRT
<213> ORGANISM: Bacteriophage

<400> SEQUENCE: 37

Lys Gln Ala Asp Ser Asn Ser Val Ala Leu Gln Tyr Ser Leu Asn Lys
1               5                   10                  15

Ala

<210> SEQ ID NO 38
<211> LENGTH: 10
<212> TYPE: PRT
<213> ORGANISM: Bacteriophage

<400> SEQUENCE: 38

Arg Leu Ser Leu Ser Ser Gly Leu Arg Leu
1               5                   10

<210> SEQ ID NO 39
<211> LENGTH: 13
<212> TYPE: PRT
<213> ORGANISM: Bacteriophage

<400> SEQUENCE: 39

Lys Arg Glu Asp Val Asn Val Thr Ser Pro Thr Lys Ser
1               5                   10
```

<210> SEQ ID NO 40
<211> LENGTH: 16
<212> TYPE: PRT
<213> ORGANISM: Bacteriophage

<400> SEQUENCE: 40

Arg Ala Glu Asn Ser Ile Thr Tyr Arg Asn Ser Ile Asn Glu Lys Val
 1               5                  10                  15

<210> SEQ ID NO 41
<211> LENGTH: 20
<212> TYPE: PRT
<213> ORGANISM: Bacteriophage

<400> SEQUENCE: 41

Arg Thr Phe His Thr Gly Gly Val Ala Gly Ser Asp Ile Thr Gln Gly
 1               5                  10                  15

Leu Pro Arg Ile
            20

<210> SEQ ID NO 42
<211> LENGTH: 16
<212> TYPE: PRT
<213> ORGANISM: Bacteriophage

<400> SEQUENCE: 42

Arg Leu Gly Ile Gln Ala Phe Glu Pro Thr Leu Val Glu Gly Arg Ala
 1               5                  10                  15

<210> SEQ ID NO 43
<211> LENGTH: 12
<212> TYPE: PRT
<213> ORGANISM: Bacteriophage

<400> SEQUENCE: 43

Arg Leu Glu Thr Thr Gln Glu Asn Ala Glu Ala His
 1               5                  10

<210> SEQ ID NO 44
<211> LENGTH: 17
<212> TYPE: PRT
<213> ORGANISM: Bacteriophage

<400> SEQUENCE: 44

Arg Ala Val His Gly Gln Leu Asn Asp Gly Gly Phe Asp Ser Gln Arg
 1               5                  10                  15

Tyr

<210> SEQ ID NO 45
<211> LENGTH: 13
<212> TYPE: PRT
<213> ORGANISM: Bacteriophage

<400> SEQUENCE: 45

Arg Leu Ser Ala Leu Gly Pro Gly Gly Leu Thr Arg Glu
 1               5                  10

<210> SEQ ID NO 46
<211> LENGTH: 14
<212> TYPE: PRT
<213> ORGANISM: Bacteriophage

<400> SEQUENCE: 46

```
Arg Val Asn Glu Phe Gly Phe Ile Glu Thr Pro Tyr Arg Lys
 1               5                  10

<210> SEQ ID NO 47
<211> LENGTH: 14
<212> TYPE: PRT
<213> ORGANISM: Bacteriophage

<400> SEQUENCE: 47

Arg Gly Tyr Leu Asn Leu Glu Glu Val Asn Ala Glu Arg Phe
 1               5                  10
```

BACTERIOPHAGE HAVING KILLING ACTIVITY SPECIFIC TO *STAPHYLOCOCCUS AUREUS*

CROSS REFERENCE TO RELATED APPLICATIONS

The present application is a National Phase Application of International Application No. PCT/KR2007/002995 filed Jun. 20, 2007, which claims priority to Korean Patent Application No. 10-2006-0055461 filed Jun. 20, 2006, which applications are incorporated herein fully by this reference.

TECHNICAL FIELD

The present invention relates to a novel bacteriophage having killing activity specific to *Staphylococcus aureus*.

BACKGROUND ART

A Bacteriophage is any one of a number of virus-like agents that infect bacteria and the term is commonly used in its shortened form, 'phage'. Bacteriophages consist of an outer protein hull enclosing genetic material. The genetic material can be single stranded or double stranded DNA or RNA. To survive, bacteriophages need a host and every bacterium has a specific partner phage. When a bacteriophage invades into a host, it duplicates itself and then induces expressions of enzymes involved in the decomposition of cell wall of the host cell. The enzymes destroy cell wall by attacking murein or peptidoglycan which is responsible for rigidity and mechanical strength of the cell wall.

A bacteriophage was first found by Twort, an English bacteriologist, in 1915 during his research on the phenomenon that *micrococcus* colony is decomposed opaque by something. And in 1917, a French bacteriologist d'Herelle found out that there was something that decomposes *Shigella disentriae* in filtrate of feces of a patient with dysentery, and he continued to study to identify the material, leading to the finding of a bacteriophage which means "eating bacteria". Since then, bacteriophages had been continuously identified specific to various pathogenic bacteria including *Shigella*, typhoid bacillus and comma bacillus. Dr. Delbruck of Caltech and some European scientists who had moved to USA during World War II focused their studies on the bacteriophage specific to *E. coli*. Since penicillin was discovered by Flemming in 1950, the antibiotic has been used widely and the research on bacteriophages has been limited to some Eastern European countries. However, multi-drug resistant pathogenic bacteria have been frequently reported since 2000, which must be resulted from the abuse and misuse of antibiotics. Based on its potential for alternative antibiotics, bacteriophages have been now in the center of the studies.

Even though antibiotics (or antibacterial agents) are still major therapeutic agents for the treatment of various infectious diseases, the antibiotics-based treatment has a serious problem. Numbers of multi-drug resistant strains have been found since 1980s, and it may be due to the excessive use of such antibiotics. In 1986, *Staphylococcus aureus* having resistance against vancomycin, which is so called 'the last antibiotic', and other multi-drug resistant strains were found, giving a great shock to those in medical field. Vancomycin resistant enterococci (VRE) was first reported in France in 1986 and first separated in USA in 1988. Since then, the cases of enterococci infection have been increased every year with high frequency, everywhere including Europe, USA, Singapore, Japan, Australia, Korea, etc, making the vancomycin resistant enterococci as a causal agent of nosocomial infections. In Korea, VRE was first isolated in 1992. Therefore, it is an urgent request to develop a novel antibiotic to treat the conventional antibiotic resistant bacteria and further to lead national health and medical techniques. To achieve the above goal, a novel antibiotic has to be developed through the completely different method. Again, it is urgently required to develop an alternative antibiotic to solve the problems of multi-drug resistant bacteria along with the abuse or misuse of the conventional antibiotics and the residual antibiotics.

Thus, the present inventors first isolated *Staphylococcus aureus* and subsequently isolated a bacteriophage that is able to kill selectively the previously isolated *Staphylococcus aureus* from the natural sources. Then, the inventors investigated the morphological, biochemical and genetic characteristics of the isolated bacteriophage to distinguish it from other bacterophages. The present inventors finally completed this invention by confirming that the *Staphylococcus aureus* specific bacteriophage isolated by the inventors can be effectively used for the prevention and treatment of the disease caused by *Staphylococcus aureus*.

DISCLOSURE

Technical Problem

It is an object of the present invention to provide a novel bacteriophage that is able to selectively kill *Staphylococcus aureus*, the causing agent of infectious diseases in human and animals.

It is another object of the present invention to provide a pharmaceutical composition for the prevention and treatment for the disease caused by *Staphylococcus aureus* containing the novel bacteriophage specific to *Staphylococcus aureus* as an active ingredient.

It is a further object of the present invention to provide an antibiotic containing the novel bacteriophage specific to *Staphylococcus aureus* as an active ingredient.

It is also an object of the present invention to provide a disinfectant containing the novel bacteriophage specific to *Staphylococcus aureus* as an active ingredient.

Technical Solution

The present invention provides a novel bacteriophage belongs to T4-like phage genus, Myoviridae family, which has killing activity specific to *Staphylococcus aureus*, excellent acid resistance and thermo-stability, and the genome represented by the nucleotide sequence selected from the group consisting of sequences represented by SEQ. ID. NO: 1-NO: 26.

*Staphylococcus aureus* is a causing agent of skin infection and food poisoning. It is a very dangerous pathogenic bacterium having strong resistance against methicillin. It was reported that *Staphylococcus aureus* isolated in Korea has resistance against to methicillin as high as 73% at average, which is the top level in the world. That means 73% of *Staphylococcus aureus* cannot be killed by methicillin and this bacterium is highly antibiotic resistant.

The present inventors have endeavored to kill *Staphylococcus aureus* selectively. And at last, the inventors isolated *Staphylococcus aureus* from pathogen and further isolated a novel bacteriophage that is able to kill the isolated *Staphylococcus aureus* selectively. This novel bacteriophage having killing activity specific to *Staphylococcus aureus*, isolated by the inventors, was deposited at Korean Agricultural Culture Collection (KACC), National Institute of Agricultural Biotechnology (NIAB) on Jun. 14, 2006 (Accession No: KACC 97001 P) and deposited at the Korean Collection for Type Cultures (KCTC), located at the Korean Research Institute of Bioscience and Biotechnology (KRIBB), #52, Oun-dong, Yusong-ku, Taejon 305-333, Republic of Korea, on Jul. 10, 2007, and given the accession number KCTC 11153BP.

The bacteriophage of the present invention has such biochemical characteristics as acid resistance and thermo-stability. According to a preferred embodiment of the present invention, the bacteriophage of the invention can survive, in fact can be stable, at the temperature of 30-40° C. and also at low temperature of 4° C. (Example 2 and FIG. 5). The bacteriophage of the invention is also stable at the pH range of 4-10 (Example 2 and FIG. 6).

The bacteriophage of the invention has not only killing activity specific to *Staphylococcus aureus* but also acid resistance and thermo-stability, so that it can be effectively used for the treatment of an animal or human with a disease caused by *Staphylococcus aureus*. The bacteriophage is not easily inactivated and maintains its killing activity stably in wide temperature and pH ranges.

The structural protein of the bacteriophage of the invention has the amino acid sequence selected from the group consisting of sequences represented by SEQ. ID. NO: 27-NO: 47.

According to a result of DNA sequencing with the genomic DNA of the bacteriophage of the invention, the bacteriophage has the nucleic acid molecule having the nucleotide sequence selected from the group consisting of sequences represented by SEQ. ID. NO: 1-NO: 26 (Example 3).

The term "nucleic acid molecule" herein includes DNA (gDNA and cDNA) and RNA, and the nucleotide, a constituent unit of the nucleic acid molecule, includes not only natural nucleotides but also analogues with modification of sugar or base (Scheit, *Nucleotide Analogs*, John Wiley, New York (1980); Uhlman and Peyman, Chemical Reviews, 90:543-584 (1990)).

The present invention also provides a pharmaceutical composition for the prevention and treatment of a disease caused by *Staphylococcus aureus* containing the aforementioned bacteriophage as an active ingredient.

The bacteriophage included in the pharmaceutical composition of the invention can kill *Staphylococcus aureus* specifically, so that it is very effective in treatment of various diseases caused by *Staphylococcus aureus*.

*Staphylococcus aureus* is the number one pathogenic bacterium to cause infectious mastitis in cattle. *Staphylococcus aureus* is found in 90% of the total dairy cows in USA and the dairy cow infected by this pathogenic bacterium in total dairy cows is estimated to be 10%. *Staphylococcus aureus* is a causing agent of acute dermatitis in human, and this acute dermatitis can be suddenly developed into sepsis taking a patient's life. *Staphylococcus aureus* is also a causing agent of pyogenic disease, sweat odor and food poisoning. Thus, the pharmaceutical composition of the present invention can be used for the treatment of various diseases caused by *Staphylococcus aureus* such as mastitis, acute dermatitis, sepsis, pyogenic disease, food poisoning, pneumonia, osteomyelitis, impetigo, bacteremia, endocarditis and enteritis. According to a preferred embodiment of the present invention, every day spray of the bacteriophage of the invention around a teat of dairy cow having mastitis could significantly reduce the symptoms of mastitis, suggesting that the bacteriophage of the invention is effective for the treatment of mastitis.

The term 'treatment' herein indicates (i) the prevention of the disease caused by *Staphylococcus aureus*; (ii) the suppression of the disease caused by *Staphylococcus aureus*; and (iii) the relief of the disease caused by *Staphylococcus aureus*.

The pharmaceutical composition of the present invention can additionally include a pharmaceutically acceptable carrier, which is exemplified by lactose, dextrose, sucrose, sorbitol, mannitol, starch, acacia rubber, calcium phosphate, alginate, gelatin, calcium silicate, microcrystalline cellulose, polyvinylpyrrolidone, cellulose, water, syrup, methyl cellulose, methylhydroxybenzoate, propylhydroxybenzoate, talc, magnesium stearate and mineral oil, but not always limited thereto. The pharmaceutical composition of the present invention can also include a lubricant, a wetting agent, a sweetener, a flavor, an emulsifier, a suspending agent, and a preservative, in addition to the above ingredients.

The pharmaceutical composition of the present invention can be applied or sprayed on the lesion, and administered orally or parenterally (for example, intravenous, intramuscular, hypodermic, local or peritoneal injection).

The effective dosage of the pharmaceutical composition of the present invention varies from the formulation, administration pathway, age, weight and gender of animal or human with a disease caused by *Staphylococcus aureus*, severity of a disease, diet, administration frequency and pathway, excretion and sensitivity. In general, the dosage can be determined by an experienced doctor with consideration of the goal of the treatment or preventive effect. According to an exemplary embodiment of the present invention, the pharmaceutical composition of the invention contains the bacteriophage at the concentration of $1\times10^3$–$1\times10^{10}$ pfu/µl.

The pharmaceutical composition of the present invention can be formulated as a unit dose medicine or as a medicine in multidose vehicle by mixing with a pharmaceutically acceptable carrier and/or excipient by the method well known to those in the art. The pharmaceutical formulation can be selected from a group consisting of ointments, solutions, suspensions or emulsions, extracts, powders, granules, tablets or capsules and additionally includes a dispersing agent or a stabilizing agent.

In another preferred embodiment of the present invention, the present invention provides an antibacterial agent for cosmetics and an antibiotic for medical use which contain the aforementioned bacteriophage as an active ingredient.

*Staphylococcus aureus* is frequently found in cosmetics along with *Bacillus subtilis, E. coli* and *Pseudomonas aeruginosa*. Cosmetics use oil or water as a major ingredient, to which glycerin and sorbitol, which are carbon sources of a microorganism, and amino acid derivatives and a protein which are nitrogen sources of a microorganism, are added, suggesting that there are enough nutrition and ingredients to attract microorganisms including bacteria. In addition, the term of use of the cosmetics is comparatively long, indicating that it is in high risk of contamination by a microorganism. To prevent color changes or odor changes caused by the contamination of a microorganism, an antibacterial agent is necessarily added to cosmetics for a long shelf-life.

A synthetic antiseptic such as parabens is widely used as an additive for cosmetics, but it is potentially dangerous. Particularly, since its accumulation in breast cancer cells was detected, it has been recognized that the accumulation of such synthetic antiseptic via cosmetics might be very harmful. The American Academy of Dermatology's Committee listed the synthetic antiseptic as the number two allergen causing skin trouble. Recently what worries us is that cosmetics for children also includes such artificial synthetic antiseptic, suggesting that children are exposed on such harmful antiseptic longer and much, raising the risk seriously. Therefore, it is sincerely requested to develop a natural antiseptic.

The bacteriophage of the present invention is characterized by its high specificity to *Staphylococcus aureus*, compared with other conventional antibiotics. That is, the bacteriophage can selectively kill *Staphylococcus aureus* only without killing useful bacteria, suggesting that it is a highly valuable antibiotic that has less side effects. The bacteriophage-based antibiotics, unlike the conventional antibiotics, do not induce resistance so that their life cyclings are comparatively long. Most conventional antibiotics are gradually limited in use because of the increasing resistance. On the other hand, the antibiotic containing the bacteriophage of the invention as an active ingredient can solve the problem of the antibiotic-resistance and thus has longer life cycling.

Therefore, the antibiotic containing the bacteriophage of the invention as an active ingredient that is able to kill *Staphylococcus aureus* selectively can be effectively used as a novel antibiotic with excellent antibacterial, bactericidal and antiseptic effects. The term 'antibiotic' is used herein as a general term for antiseptics, bactericidal agents and antibacterial agents.

In another preferred embodiment of the present invention, the invention provides a disinfectant containing the aforementioned bacteriophage as an active ingredient.

The distribution of bacteria isolated from nosocomial infection has been changed over time. According to a report of NNIS (National Nosocomial Infection Surveillance System), USA, Gram-positive bacteria particularly *Staphylococcus aureus* have been increasing in number among those isolated bacteria since late 1980s, and this phenomenon is consistent with that in Korea. According to a report made in Korea, the dominant distribution is *E. coli, Pseudomonas aeruginosa*, coagulase negative *Staphylococcus* and *Staphylococcus aureus* follows in that order. But, the isolation of *Staphylococcus aureus* is increasing gradually. Korean Society for Nosocomial Infection Control (KSNIC) reported in 1996 that *Staphylococcus aureus* took 17.2% of total isolated pathogenic microorganisms and *Pseudomonas aeruginosa* (13.8%) and *E. coli* (12.3%) followed. And, 78.8% of the total *Staphylococcus aureus* isolated were confirmed to have resistance against antibiotics.

Based on the above finding, the disinfectant containing the bacteriophage of the present invention that is able to kill specifically *Staphylococcus aureus* can be effectively used as a disinfectant specifically for hospitals and public health. It is also available as a general life disinfectant, a food and kitchen disinfectant, and a stall disinfectant.

DESCRIPTION OF DRAWINGS

The application of the preferred embodiments of the present invention is best understood with reference to the accompanying drawings, wherein:

FIG. 1 is a schematic diagram illustrating the isolation method of the bacteriophage having killing activity specific to *Staphylococcus aureus*;

FIG. 2 is a photograph showing the result of plaque assay for detection of a bacteriophage specific to *Staphylococcus aureus*;

FIG. 3 is an electron microphotograph showing the *Staphylococcus aureus* specific bacteriophage isolated through plaque assay;

FIG. 4 is a diagram illustrating the isolated bacteriophage adsorption to the isolated *Staphylococcus aureus*;

FIG. 5 is a diagram illustrating the thermo-stability of the isolated bacteriophage; (A) is illustrating the thermo-stability of the bacteriophage at different temperatures; and (B) is illustrating the thermo-stability of the bacteriophage against cold-shock generated by the addition of a cold medium;

FIG. 6 is a diagram illustrating the acid resistance of the isolated bacteriophage;

FIG. 7 is a diagram illustrating the result of one-dimensional electrophoresis with the structural protein of the isolated bacteriophage;

FIG. 8 is a diagram illustrating the characteristics of the genome extracted from the isolated bacteriophage; lane 1: non-treated genome, lane 2: genome treated with DNase I, lane 3: genome treated with RNase A, lane 4: genome treated with mung bean nuclease, and lane M: molecular marker;

FIG. 9 is a diagram illustrating the fragmentation profiles of the genome extracted from the isolated bacteriophage by restriction enzymes; lane M: molecular marker, lane 5: fragmentation profile by Sau3AI, lane 6: fragmentation profile by TaqI, lane 7: fragmentation profile by MspI, lane 8: fragmentation profile by MboI, lane 9: fragmentation profile by CivAII, lane 10: fragmentation profile by Tsp5091, lane 11: fragmentation profile by sac I, lane 12: fragmentation profile by Sac II, lane 13: fragmentation profile by HindIII, lane 14: fragmentation profile by HindII, lane 15: fragmentation profile by XhoI, lane 16: fragmentation profile by XbaI, and lane 17: fragmentation profile by AccI;

FIG. 10 is a schematic diagram illustrating the construction procedure of the bacteriophage genomic DNA library;

FIG. 11 is a diagram illustrating the selection of the recombinant plasmid;

FIG. 12 is a diagram illustrating the result of gene analysis with NCBI Blast program;

FIG. 13 is a contig map based on the result of gene analysis;

FIG. 14 is a diagram illustrating the result of open reading frame analysis using NCBI Blast and Vector. NTI ContigExpress programs.

BEST MODE

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Isolation of *Staphylococcus aureus* from a Pathogen and Isolation of the Bacteriophage Having Killing Activity Specific to *Staphylococcus aureus*

<1-1> Isolation of *Staphylococcus aureus*

Bacteriophages generally live together with bacteria in natural system. To isolate the bacteriophage specifically infecting *Staphylococcus aureus*, samples were collected from everywhere where the inventors expected *Staphylococcus aureus* lives. To investigate the samples where *Staphylococcus aureus* really exists, the Baird-Parker agar medium, a *Staphylococcus aureus* selection medium, was used.

Particularly, the present inventors selected dairy cow mastitis as a target disease to isolate *Staphylococcus aureus*, the target microorganism. Mastitis is one of the most representative diseases caused by *Staphylococcus aureus*. A sample was taken from milk of a dairy cow with mastitis and *Staphylococcus aureus* was isolated therefrom using the Baird-Parker agar medium, a *Staphylococcus aureus* selection medium. The isolated *Staphylococcus aureus* was identified as *Staphylococcus aureus* by biochemical analysis including Gram staining method, catalase test and analysis with Vitek of bioMeriuex. The results are shown in Table 1.

TABLE 1

| Vitek ID | 200000-0 (A1-18) catalase + Coagulase + |
| Type | Gram positive identification card (GPI) |
| Condition | Final |
| Time | 5 hours |
| Organism | Staphylococcus aureus |

| PB+ | BAC− | OPT+ | HCS+ | 6NC+ | 10B+ |
|---|---|---|---|---|---|
| 40B− | ESC− | ARG− | URE− | TZR+ | NOV− |
| DEX+ | LAC+ | MAN+ | RAF− | SAL− | SOR− |
| SUC+ | TRE+ | ARA− | PYR+ | PUL− | INU− |
| MEL− | MLZ− | CEL− | RIB− | XYL− | CAT+ |
| BH/CO+ | | | | | |

<1-2> Isolation of the *Staphylococcus aureus* Specific Bacteriophage

To isolate a bacteriophage specific to the isolated *Staphylococcus aureus*, samples expected to contain the bacteriophage were cultured together with *Staphylococcus aureus*. The culture solution was centrifuged, filtered and then cultured again with *Staphylococcus aureus*, the bait for the isolation of a bacteriophage, and then lysis of *Staphylococcus aureus* was investigated. The lysis was finally verified by plaque assay.

Particularly, to isolate the bacteriophage having killing activity specific to *Staphylococcus aureus*, samples were collected from soil and straw in a cowshed and sewage where the bacteriophage was expected to be. These samples were cocultivated with the previously isolated *Staphylococcus aureus* at 37° C. for 3-4 hours. After cultivation, the culture broth was centrifuged for 20 minutes at 8,000 rpm. The supernatant was filtered with a 0.45 μm filter. With resultant filtrate, the *Staphylococcus aureus* specific bacteriophage was isolated by plaque assay. The method used for isolation of the *Staphylococcus aureus* specific bacteriophage is shown in the schematic diagram of FIG. 1. To observe the morphology of the obtained bacteriophage, CsCl density gradient (density: 1.15 g/ml, 1.45 g/ml, 1.50 g/ml and 1.70 g/ml) centrifugation (38,000 rpm, 22 hours, 4° C.) was performed, leading to the purification of the bacteriophage. The purified bacteriophage was loaded in a cupper grid, followed by negative staining with 2% uranyl acetate and drying. The morphology was observed under electron microscoph. As a result, the isolated bacteriophage was confirmed to be the one belonging to T4-like phage genus, Myoviridae family according to the morphological classification method (FIG. 3).

Example 2

Characteristics of the *Staphylococcus aureus* Specific Bacteriophage Isolated

The obtained bacteriophage was tested for adsorption to its host, thermo-stability and acid resistance to define the biochemical characteristics. The basic media for the analysis were a TSB (tryptic soy broth) medium (casein digest, 17 g/l; soybean digest, 3 g/l; dextrose, 2.5 g/l; NaCl, 5 g/l; dipotassium phosphate, 2.5 g/l) which is a liquid medium for bacteria culture and a phage liquid medium (Bacto-peptone, 15 g/l; trypton, 8 g/l; bacto-yeast extract, 1 g/l; NaCl, 30 g/l; 1 mM $MgSO_4$; 0.1 mM $CaCl_2$; pH 7.2).

<2-1> Adsorption to Bacteria

To investigate bacteriophage adsorption to bacteria, 1 in of $10^8$ cfu/ml *Staphylococcus aureus* solution was first mixed with 1 ml of $10^8$ pfu/ml bacteriophage solution. The mixture was incubated at 37° C., during which 100 μl of the mixture was taken every 5 minutes. The obtained 100 μl of the mixture was 100 fold-diluted in the liquid medium for bacteria culture. Centrifugation was performed at 5,000 rpm for 10 minutes to precipitate *Staphylococcus aureus* only. After centrifugation, the 100 μl of supernatant containing the bacteriophage which was not adhered onto *Staphylococcus aureus* was recovered. From this, 5 μl was taken again. The number of bacteriophage non-adhered to *Staphylococcus aureus* in the 5 μl sample was counted to investigate when the bacteriophage was adhered to *Staphylococcus aureus*. As a result, bacteriophage was mostly adhered to the bacteria between 5 and 15 minutes from mixing (FIG. 4).

<2-2> Thermo-Stability

To investigate the thermo-stability of the bacteriophage at different temperatures, $10^6$ pfu/ml of bacteriophage solution was first prepared and then six 900 μl media were prepared. Six 900 μl media were incubated at different temperatures of 30, 37, 40, 50, 60 and 70° C. for minutes, to which $10^6$ pfu/ml of the bacteriophage solution was added by 100 μl piper medium, followed by further incubation for 10 minutes. 100 μl was obtained therefrom and loaded on plate media by 5 μl per medium, followed by culture at 37° C. for overnight. After cultivation, the number of the bacteriophage survived was counted. At that time, the number of the bacteriophage survived at 37° C. was regarded as a standard. As a result, the bacteriophage was most stable at 30-40° C. and the survival rate decreased at the temperature higher than 40° C. (FIG. 5 (A)).

Thermo-stability to cold shock (performed by adding a cold medium) was investigated. The temperature of a 4.5 ml medium was maintained at 60° C. and then 500 μl of $10^6$ pfu/ml of bacteriophage solution was added thereto. 100 μl sample was taken every 10 minutes for one hour and then diluted in cold bacterial culture medium (4° C.). The number of bacteriophage in 5 μl diluted sample was counted by the same manner as described above and compared with the standard (the number of bacteriophage survived at 37° C.). As a result, the bacteriophage was stable to cold shock up to 10-20 minutes, but after then the bacteriophage became unstable (FIG. 5 (B)).

<2-3> Acid Resistance

Acid resistance of the isolated bacteriophage was investigated by the similar manner as performed for the thermo-stability investigation. Survival rate of the bacteriophage was investigated in a medium in which pH was adjusted to 7.0, and the obtained value was considered as a standard. To test acid resistant, pH of each medium was respectively regulated to 3.0-10.0 (pH=3, 4, 5, 6, 7, 8, 9 and 10). 900 μl of sample solution was taken from each medium with different pH. 100 μl of $10^6$ pfu/ml of bacteriophage solution was added thereto. The mixture was incubated at 37° C. for 10 minutes. After incubation, the number of the bacteriophage survived at each pH was counted by the same manner as described above. As a result, the bacteriophage was most stable at pH 5-8, and somewhat stable at pH 4, 9 and 10 but became unstable at pH 3 (FIG. 6).

<2-4> Structural Protein of the Isolated Bacteriophage

To investigate the structural protein of the isolated bacteriophage, one-dimensional electrophoresis was performed. To obtain the protein composing the outer envelope of the bacteriophage, 250 μl of the bacteriophage solution was cultured. The bacteriophage was concentrated (250×) by using 1 in of 20% polyethylene glycol 8000/2.5 M NaCl aqueous solution. 200 μl of the concentrated bacteriophage sample and 800 μl of acetone were mixed vigorously and then the mixture was standing at −20° C. for 10 minutes. The mixture was centrifuged at 4° C., with 3,200 rpm for 20 minutes, followed by removal of supernatant and air drying of the resultant precipitate. The precipitate was resuspended in 50 μl of 5× electrophoresis sample buffer, followed by boiling for 5 minutes. The prepared sample was subjected to one-dimensional electrophoresis. As a result, as shown in FIG. 7, a group of proteins having around 50, 60, 90, 120 and 150 kDa was confirmed. Those proteins were cut off from a gel and short peptide sequencing based on liquid chromatography-mass spectropy (LC-MS) was carried out. The obtained amino acid sequence was analyzed by using NCBI Blast (Virus Org.) program. As a result, the amino acid sequence obtained was identified as the amino acid sequence of the protein forming the outer envelope of the bacteriophage. The result of the amino acid sequencing is as follows.

(1) Amino Acid Sequences of Around 50 kDa Protein

```
SEQ. ID. NO: 27:   (R)  ARAAAENIIPNSTGAAK (A)

SEQ. ID. NO: 28:   (R)  AAAENIIPNSTGAAK (A)

SEQ. ID. NO: 29:   (K)  LLDYAEAGDNIGALLR (G)

SEQ. ID. NO: 30:   (R)  SIGSNIADAVKK (V)

SEQ. ID. NO: 31:   (R)  KASLSGLR (C)

SEQ. ID. NO: 32:   (R)  INEVTQDYLQVRINK (L)
```

(2) Amino Acid Sequences of Around 60 kDa Protein

```
SEQ. ID. NO: 33:   (K)  KAGLAVGASYYHFK (T)

SEQ. ID. NO: 34:   (K)  DLNVVDHVLKHDR (L)

SEQ. ID. NO: 35:   (K)  TIKTEVDPLMTR (A)

SEQ. ID. NO: 36:   (K)  TNTVNSSKLNTPK (N)
```

(3) Amino Acid Sequences of Around 90 kDa Protein

```
SEQ. ID. NO: 37:   (K)  QADSNSVALQYSLNK (A)

SEQ. ID. NO: 38:   (R)  LSLSSGLR (L)

SEQ. ID. NO: 39:   (K)  REDVNVTSPTK (S)

SEQ. ID. NO: 40:   (R)  AENSITYRNSINEK (V)
```

(4) Amino Acid Sequences of Around 120 kDa Protein

```
SEQ. ID. NO: 41:   (R)  TFHTGGVAGSDITQGLPR (I)

SEQ. ID. NO: 42:   (R)  LGIQAFEPTLVEGR (A)

SEQ. ID. NO: 43:   (R)  LETTQENAEAH (-)

SEQ. ID. NO: 44:   (R)  AVHGQLNDGGFDSQR (Y)
```

(5) Amino Acid Sequences of Around 150 kDa Protein

```
SEQ. ID. NO: 45:   (R)  LSALGPGGLTR (E)

SEQ. ID. NO: 46:   (R)  VNEFGFIETPYR (K)

SEQ. ID. NO: 47:   (R)  GYLNLEEVNAER (F)
```

Example 3

Genetic Characteristics of the *Staphylococcus aureus* Specific Bacteriophage Isolated To identify the isolated bacteriophage, genotype and gene sequence of the genome extracted from it were analyzed. First, genome of the bacteriophage was extracted by the conventional method and the structural property of the genome was investigated.

Particularly, 200 ml of TSB medium, 50 ml of *Staphylococcus aureus* suspension ($OD_{600}$=1) and 1 ml of filtered bacteriophage solution at the concentration of $10^8$ pfu/ml were added into a 1 l flask, followed by shaking-culture at 37° C. for 3-4 hours. Then, lysis of *Staphylococcus aureus* was observed. After confirming lysis, the culture solution was filtered with a 0.45 μm filter. After fitration, 20% polyethylene glycol 8000/2.5 M NaCl aqueous solution was added to the filtrate by the volume of ⅙ of the total volume of the filtrate, and the mixture was standing at 4° C. for overnight. Centrifugation was performed at 8,000 rpm for 20 minutes to obtain the bacteriophage pellet. The obtained bacteriophage precipitate was resuspended in 1 ml of phosphate buffer saline (PBS), to which 20% polyethylene glycol 8000/2.5 M NaCl aqueous solution was added again by the volume of ⅙ of the total volume of the resuspenssion solution. The mixture was standing at 4° C. again for one hour. One hour later, centrifugation was performed at 14,000 rpm for 10 minutes to obtain the purified bacteriophage precipitate. The precipitate was mixed with 200 μl of iodide buffer (10 mM Tris-HCl (pH 8.0), 1 mM EDTA, 4 M NaI). The mixture was standing at room temperature for 15 minutes, followed by extraction of the genome of the isolated bacteriophage by using DNeasy Tissue kit (Qiagen) and PCR purification kit (Labopass). To confirm whether the extracted genome of the bacteriophage was DNA or RNA, the genome was treated with DNase I (10 U/μl) and RNase A (10 μg/μl) at 37° C. for one hour, respectively. The genome was separatedly treated with mung bean nuclease (45 U/μl) for 15 minutes at room temperature to determine whether it was a single stranded DNA or a double-stranded DNA, in case it would be confirmed to be DNA. After enzymatic treatment, electrophoresis was performed with those prepared samples using 0.8% agarose gel and fragmentation pattern by each enzyme was investigated. As a result, the obtained genome was sensitive to DNase I and mung bean nuclease (FIG. 8). The sensitivity to DNase I indicates that the genome is DNA and the sensitivity to mung bean nuclease indicates that the genome is a double stranded DNA. Therefore, it was confirmed that the genome of the isolated bacteriophage is a double stranded DNA.

The genome extracted from the bacteriophage is a genomic DNA (gDNA). To analyze the gene sequence of the gDNA, the genome was treated with different restriction enzymes and fragmentation patterns by different restriction enzymes were observed. And the results are shown in FIG. 9. From the result, MspI was considered to be most appropriate for the construction of gDNA library. Thus, gDNA library was constructed by the conventional method using MspI-treated gene fragments. The method for the construction of gDNA library is shown in FIG. 10.

Particularly, partial digestion by a specific restriction enzyme (Msp I was used herein) is essential to obtain various gene fragments. According to the previous experiments, the treatment of the genome with MspI for one minute at 30° C. is appropriate for the construction of gDNA library. Thus, the fragments of gDNA of the bacteriophage were obtained by the foregoing partial digestion. The obtained fragments were introduced into pBluescript II SK(+) phagemid vector (Stratagene) using T4 ligase. The resultant recombinant plasmid having the fragment of the bacteriophage gene was introduced into *E coli* Top10F' via electroporation, a kind of electro-transformation. The transformant with the recombinant plasmid was selected on the agar plate medium containing ampicillin supplemented with X-Gal (5-bromo-4-chloro-3-indolyl-beta-D-galactopyranoside) and isopropyl β-D-1-thiogalacto-pyranoside (IPTG) through Blue-White colony selection method. The selected single colony was inoculated into the liquid medium containing ampicillin, followed by shaking-culture for overnight. After cultivation, plasmids were extracted from the culture cells using a plasmid purification kit (iNtRON). The extracted plasmids were electrophoresed using 0.8% agarose gel to confirm the size. Based on the size, a recombinant plasmid was selected. The selection procedure is shown in FIG. 11. The selected plasmids were 51 in total and thus clones obtained were also 51. The clones were cultured again and plasmids were extracted from the culture cells by the same manner as described above and nucleotide sequencing with the extracted plasmids was performed. For the nucleotide sequencing, the common sequencing primers, M13 forward primer represented by SEQ. ID. NO: 48 and M13 reverse primer represented by SEQ. ID. NO: 49, were used. As a result, the obtained gene sequences were the partial sequence forming the total genome of the isolated bacteriophage, which were represented by SEQ. ID. NO: 1-NO: 26.

The nucleotide sequences obtained above were analyzed by using NCBI Blast program and the result is shown in FIG. 12. Based on the analyzed nucleotide sequences of the bacteriophage, contig map was constructed to found the exact location of the analyzed nucleotide sequence on the full genome (FIG. 13). To understand the genetic functions of the nucleotide sequences, open reading frame (ORF) analysis was performed using NCBI Blast and Vector NTI ContigExpress programs (INFORMAX). And the results are shown in FIG. 14.

Example 4

An Example of the Application of the *Staphylococcus aureus* Specific Bacteriophage for the Prevention of *Staphylococcus aureus* Infection 100 μl of the bacteriophage solution ($10^8$ pfu/ml) was added into 9 μl of nutrient broth (beef extract 3 g/t, peptone 5 g/l). A control medium was prepared without the addition of the bacteriophage solution. 100 μl of *Staphylococcus aureus* solution ($10^8$ cfu/ml) was added into each medium, followed by investigation of the growth of *Staphylococcus aureus*. In the medium not containing the bacteriophage solution, *Staphylococcus aureus* was growing so well. On the other hand, in the nutrition broth containing the bacteriophage solution, *Staphylococcus aureus* was not grown at all. It was confirmed from the above result that the bacteriophage isolated in example 1 was very effective in the prevention of the infection of *Staphylococcus aureus*.

Example 5

An Example of the Application of the *Staphylococcus aureus* Specific Bacteriophage for the Treatment of an Infectious Disease Caused by *Staphylococcus aureus*

10 dairy cows with mastitis caused by *Staphylococcus aureus* were selected to investigate the effect of the bacteriophage isolated in example 1 on mastitis. The cows were divided into two groups (5 cows per group). 10 in of bacteriophage solution ($10^8$ pfu/ml) was sprayed on one group every day and 10 ml of PBS without the bacteriophage was sprayed on the other group every day, particularly on the infected regions. The spray was continued for 10 days. As a result, significant treatment effect was observed in the group sprayed with the bacteriophage solution. From the result, it was confirmed that the bacteriophage isolated in example 1 was very effective in the treatment of the infectious disease caused by *Staphylococcus aureus*.

INDUSTRIAL APPLICABILITY

As explained hereinbefore, the present invention provides a novel bacteriophage that is able to kill specifically *Staphylococcus aureus*, a pathogenic microorganism. The bacteriophage of the invention can be effectively used in a variety of fields as a pharmaceutical composition for the prevention and treatment of infectious diseases caused by *Staphylococcus aureus*, as an antibacterial agent for cosmetics, as a natural antiseptic, and as a multi-purpose disinfectant.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

[Receipt of a Deposit of Microorganism]

The invention claimed is:

1. An isolated bacteriophage belonging to Myoviridae family, which has killing activity specific to *Staphylococcus aureus*, and the genome comprises sequences of SEQ ID. NOs:1-26.

2. The isolated bacteriophage according to claim 1, wherein the isolated bacteriophage is the one that was deposited under the Accession No: KACC 97001P.

3. A pharmaceutical composition for the treatment of a disease caused by *Staphylococcus aureus*, containing the isolated bacteriophage of claim 1 as an active ingredient.

4. The pharmaceutical composition according to claim 3, wherein the disease caused by *Staphylococcus aureus* is selected from the group consisting of mastitis, acute dermatitis, sepsis, pyogenic disease, food poisoning, pneumonia, osteomyelitis, impetigo, bacteremia, endocarditis and enteritis.

5. An antibiotic containing the isolated bacteriophage of claim 1 as an active ingredient.

6. A disinfectant containing the isolated bacteriophage of claim 1 as an active ingredient.

7. An antibiotic containing the isolated bacteriophage of claim 2 as an active ingredient.

8. A disinfectant containing the isolated bacteriophage of claim 2 as an active ingredient.

9. A pharmaceutical composition for the treatment of a disease caused by *Staphylococcus aureus*, containing the isolated bacteriophage of claim 2 as an active ingredient.

10. The pharmaceutical composition according to claim 9, wherein the disease caused by *Staphylococcus aureus* is selected from the group consisting of mastitis, acute dermatitis, sepsis, pyogenic disease, food poisoning, pneumonia, osteomyelitis, impetigo, bacteremia, endocarditis and enteritis.

* * * * *